United States Patent
Kobayashi et al.

(10) Patent No.: US 8,993,158 B2
(45) Date of Patent: Mar. 31, 2015

(54) NONAQUEOUS ELECTROLYTE SOLUTION CONTAINING SILYL ESTER GROUP-CONTAINING PHOSPHONIC ACID DERIVATIVE, AND LITHIUM SECONDARY BATTERY

(75) Inventors: Takeshi Kobayashi, Ichihara (JP); Shigeru Mio, Chiba (JP); Hidenobu Nogi, Chiba (JP); Takashi Hayashi, Ichihara (JP)

(73) Assignee: Mitsui Chemicals, Inc., Tokyo (JP)

( * ) Notice: Subject to any disclaimer, the term of this patent is extended or adjusted under 35 U.S.C. 154(b) by 155 days.

(21) Appl. No.: 13/699,187

(22) PCT Filed: May 17, 2011

(86) PCT No.: PCT/JP2011/061331
§ 371 (c)(1),
(2), (4) Date: Nov. 20, 2012

(87) PCT Pub. No.: WO2011/145623
PCT Pub. Date: Nov. 24, 2011

(65) Prior Publication Data
US 2013/0071732 A1    Mar. 21, 2013

(30) Foreign Application Priority Data
May 21, 2010   (JP) ................................. 2010-117404

(51) Int. Cl.
*H01M 10/05* (2010.01)
*H01M 10/0564* (2010.01)
(Continued)

(52) U.S. Cl.
CPC ........ *H01M 10/0564* (2013.01); *H01M 10/052* (2013.01); *H01M 10/0567* (2013.01); *C07F 19/005* (2013.01); *Y02E 60/122* (2013.01); *Y02T 10/7011* (2013.01); *H01M 2300/0025* (2013.01)
USPC ........................... 429/203; 429/188; 252/62.2

(58) Field of Classification Search
CPC ......... H01M 6/14; H01M 4/16; H01M 10/05; H01M 10/052; H01M 10/056; H01M 10/0563; H01M 10/0564; H01M 10/0566; H01M 10/0568; H01M 10/0569
See application file for complete search history.

(56) References Cited

U.S. PATENT DOCUMENTS 7,494,746 B2   2/2009   Tarnopolsky
2007/0048623 A1*   3/2007   Park et al. ..................... 429/326
(Continued)

FOREIGN PATENT DOCUMENTS

CN    1720293 A    1/2006
CN    1921210 A    2/2007
(Continued)

OTHER PUBLICATIONS

Richardson, Douglas D.; Caruso, Joseph A.(Derivatization of Organophosphorus Nerve Agent Degradation Products for Gas Chromoatography with ICPMS and TOF-MS Detection, Analytical and Bioanalytical Chemistry, 2007, 388(4), 809-823).*

(Continued)

*Primary Examiner* — Ula C Ruddock
*Assistant Examiner* — Scott J Chmielecki
(74) *Attorney, Agent, or Firm* — Buchanan, Ingersoll & Rooney PC

(57) ABSTRACT

The present invention provides a non-aqueous electrolyte solution which contains a silyl ester group-containing phosphonic acid derivative.

12 Claims, 1 Drawing Sheet

(51) Int. Cl.
*H01M 10/052* (2010.01)
*H01M 10/0567* (2010.01)
*C07F 19/00* (2006.01)

(56) References Cited

U.S. PATENT DOCUMENTS

| | | | |
|---|---|---|---|
| 2008/0138715 | A1 | 6/2008 | Ihara et al. |
| 2009/0325065 | A1 | 12/2009 | Fujii et al. |

FOREIGN PATENT DOCUMENTS

| | | | |
|---|---|---|---|
| JP | 5-013088 | A | 1/1993 |
| JP | 11-219711 | A | 8/1999 |
| JP | 2000-164251 | A | 6/2000 |
| JP | 2001-319685 | A | 11/2001 |
| JP | 2001-351681 | A | 12/2001 |
| JP | 2006-004746 | A | 1/2006 |
| JP | 2007-103214 | A | 4/2007 |
| JP | 2007-173113 | A | 7/2007 |
| JP | 2007-299542 | A | 11/2007 |
| JP | 2008-066062 | A | 3/2008 |
| JP | 2008-130544 | A | 6/2008 |
| JP | 2008-146929 | A | 6/2008 |
| JP | 2009-224258 | A | 10/2009 |
| KR | 10-2007-0023451 | A | 2/2007 |

OTHER PUBLICATIONS

International Search Report (PCT/ISA/210) issued on Aug. 16, 2011, by the Japanese Patent Office as the International Searching Authority for International Application No. PCT/JP2011/061331.
Written Opinion (PCT/ISA/237) issued on Aug. 16, 2011, by the Japanese Patent Office as the International Searching Authority for International Application No. PCT/JP2011/061331.
Office Action (Notification for Filing Opinion) dated Nov. 18, 2013, by the Korean Patent Office in corresponding Korean Patent Application No. 10-2012-7029905, and a Partial English Translation thereof. (13 pages).
Office Action (First Notice of Reasons for Rejection) dated Jun. 30, 2014, issued in corresponding Chinese Patent Application No. 201180024139.4, and a Partial English Translation thereof. (9 pages).
Office Action (Notice of Opinion of Second Examination) dated Dec. 29, 2014, issued in corresponding Chinese Patent Application No. 201180024139.4, and a Partial English Translation thereof. (9 pages).

* cited by examiner

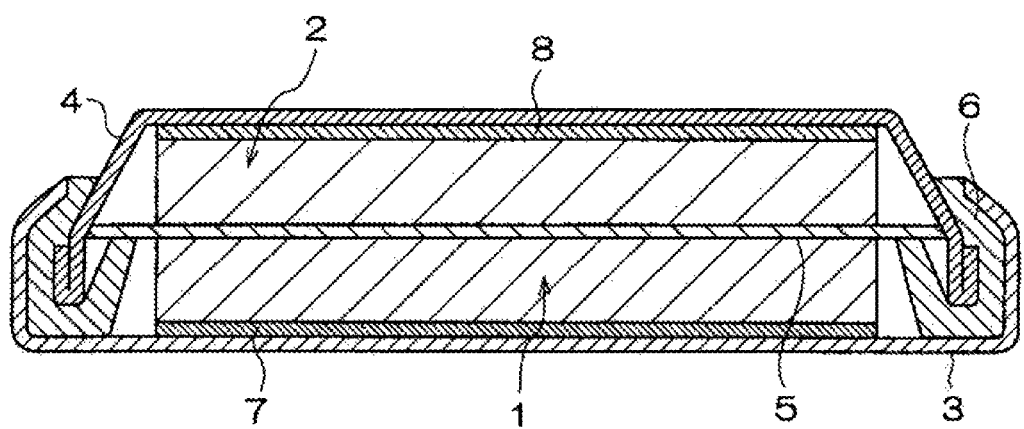

NONAQUEOUS ELECTROLYTE SOLUTION CONTAINING SILYL ESTER GROUP-CONTAINING PHOSPHONIC ACID DERIVATIVE, AND LITHIUM SECONDARY BATTERY

TECHNICAL FIELD

The present invention relates to a non-aqueous electrolyte solution having excellent output characteristics; a lithium secondary battery utilizing the non-aqueous electrolyte solution; and an additive for lithium secondary batteries which is useful as an additive for electrolyte solutions. More particularly, the present invention relates to a non-aqueous electrolyte solution which comprises, as a specific component, a phosphonic acid derivative containing at least a silyl ester group; and a lithium secondary battery utilizing the non-aqueous electrolyte solution.

BACKGROUND ART

In recent years, the application range of lithium secondary battery (hereinafter, also referred to as "lithium-ion secondary battery") has been increasingly broadened not only in portable electronic devices such as mobile telephones and laptop computers, but also as a large power source for electric cars and electric power storage. Particularly recently, there is a strong demand for a battery that can be installed in hybrid cars and electronic cars and has high capacity, high output and high energy density.

Such lithium-ion secondary battery is mainly constituted by a negative electrode composed of lithium metal and/or a carbon material (such as graphite) having excellent lithium absorbing and releasing properties; a positive electrode composed of a complex oxide of lithium and a transition metal; and a non-aqueous electrolyte solution.

Examples of positive electrode active material used in such positive electrode include lithium metal oxides such as $LiCoO_2$, $LiMnO_2$, $LiNiO_2$ and $LiFePO_4$.

Furthermore, as the non-aqueous electrolyte solution, for example, a solution in which a lithium salt such as $LiPF_6$, $LiBF_4$, $LiN(SO_2CF_3)_2$ or $LiN(SO_2C_2F_5)_2$ is added to a mixed solvent of a highly dielectric cyclic carbonate, such as propylene carbonate or ethylene carbonate, and a low-viscosity chain carbonate, such as diethyl carbonate, methylethyl carbonate or dimethyl carbonate, is generally used.

Meanwhile, as negative electrode active material used in the negative electrode, lithium metal, metal compounds (such as elemental metals, oxides and alloys formed with lithium) that are capable of absorbing and releasing lithium and carbon materials are known and, in particular, lithium-ion secondary batteries utilizing a coke, artificial graphite and/or natural graphite, which is capable of absorbing and releasing lithium, have been put into practical use.

In recent years, in terms of the battery performance, not only a high capacity but also a high output are desired; therefore, there is a demand for a method of reducing the battery resistance under a variety of conditions.

As a factor of increasing the battery resistance, film formation on the surface of the negative electrode by a degradation product of the solvent or an inorganic salt, which is caused by reductive decomposition reaction of the electrolyte solution, is considered. When such reductive reaction occurs continuously, the film amount is increased and the battery resistance is consequently increased, so that the charge-discharge efficiency is decreased and the energy which can be extracted from the battery is reduced.

Furthermore, other problems to be solved include deterioration of the battery performance in a high-temperature environment. Deterioration of a lithium-ion secondary battery in a high-temperature environment is caused by a variety of factors such as degradation of lithium transition metal oxide, degradation of the electrolyte solution and destruction of the film formed on the negative electrode surface. Therefore, there is also a demand for a method of inhibiting such deterioration of the battery performance in a high-temperature environment.

In order to solve these problems, it has been attempted to improve the storage properties and resistance of a battery by adding vinylene carbonate (VC) to a non-aqueous electrolyte solution (see, for example, Japanese Patent Application Laid-Open (JP-A) No. H5-13088).

Furthermore, there have been proposed techniques for allowing a non-aqueous electrolyte solution to contain a compound having phosphorus (P) as a constituent element. Examples of such compound include chain phosphonic acid esters (see, for example, JP-A No. 2009-224258, JP-A No. 2000-164251 and JP-A No. II11-219711), cyclic anhydrides of phosphonic acid (see, for example, JP-A No. 2008-66062), cyclic phosphonic acid esters (see, for example, JP-A No. 2001-351681) and phosphoric acid silyl esters (see, for example, JP-A No. 2001-319685).

SUMMARY OF INVENTION

Technical Problem

However, vinylene carbonate (VC) cannot be said to be sufficient from the viewpoint of inhibiting an increase in the battery resistance. Furthermore, conventional compounds having phosphorus (P) as a constituent element also cannot be said to be sufficient from the viewpoints of inhibiting an increase in the battery resistance, and inhibiting deterioration of performance in a high-temperature environment; therefore, a further improvement is required.

The present invention was made in view of the above-described problems and an object of the present invention is to provide a non-aqueous electrolyte solution which can improve the output characteristics of a battery by reducing the battery resistance, and inhibit deterioration of performance in a high-temperature environment; a lithium secondary battery utilizing the non-aqueous electrolyte solution; and an additive for lithium secondary batteries which is useful for the non-aqueous electrolyte solution.

Solution to Problem

In the process of investigation carried out to solve the above-described problems, the present inventors discovered that the battery resistance can be reduced and the storage properties in a high-temperature environment can be improved by an addition of a silyl ester group-containing phosphonic acid derivative, thereby completing the present invention.

That is, specific means for solving the above-described problems are as follows.

<1> A non-aqueous electrolyte solution, comprising a silyl ester group-containing phosphonic acid derivative.

<2> The non-aqueous electrolyte solution according to <1>, wherein the silyl ester group-containing phosphonic acid derivative is a compound represented by the following Formula (1):

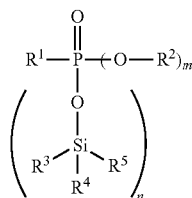
(1)

wherein, in the Formula (1), m represents 0 or 1; n represents 1 or 2; m+n=2;

$R^1$ represents a hydrogen atom, an alkyl group having 1 to 12 carbon atoms, a haloalkyl group having 1 to 12 carbon atoms, an aryl group having 6 to 14 carbon atoms (which may be substituted with a halogen atom, an alkyl group having 1 to 6 carbon atoms or a haloalkyl group having 1 to 6 carbon atoms), an alkenyl group having 2 to 12 carbon atoms, an alkyl group having 1 to 6 carbon atoms, which is substituted with at least one —$SiR^{18}R^{19}R^{20}$ group (wherein $R^{18}$, $R^{19}$ and $R^{20}$ each independently represent an alkyl group having 1 to 6 carbon atoms, an alkenyl group having 2 to 6 carbon atoms, an alkoxy group having 1 to 6 carbon atoms or a phenyl group), a haloalkyl group having 1 to 6 carbon atoms, which is substituted with at least one —$SiR^{18}R^{19}R^{20}$ group (wherein $R^{18}$, $R^{19}$ and $R^{20}$ each independently represent an alkyl group having 1 to 6 carbon atoms, an alkenyl group having 2 to 6 carbon atoms, an alkoxy group having 1 to 6 carbon atoms or a phenyl group), a 5- or 6-membered heterocyclic group (which may or may not be substituted), or a group represented by any one of the following Formulae (3-1) to (3-10);

$R^2$ represents a hydrogen atom, an alkyl group having 1 to 6 carbon atoms, a haloalkyl group having 1 to 6 carbon atoms, an alkenyl group having 2 to 6 carbon atoms, or a phenyl group (which may be substituted with a halogen atom, an alkyl group having 1 to 6 carbon atoms or a haloalkyl group having 1 to 6 carbon atoms);

$R^3$ represents an alkyl group having 1 to 6 carbon atoms, an alkenyl group having 2 to 6 carbon atoms, an alkoxy group having 1 to 6 carbon atoms, a phenyl group, a —$O$—$SiR^6R^7R^8$ group (wherein $R^6$, $R^7$ and $R^8$ each independently represent an alkyl group having 1 to 6 carbon atoms, an alkenyl group having 2 to 6 carbon atoms, an alkoxy group having 1 to 6 carbon atoms or a phenyl group), or a group in which, when n is 2, two $R^3$s are linked with each other to form —$O$—, an alkylene group having 1 to 3 carbon atoms or —$O$—$(SiR^{16}R^{17}$—$O)_p$— (wherein $R^{16}$ and $R^{17}$ independently represent an alkyl group having 1 to 6 carbon atoms, an alkenyl group having 2 to 6 carbon atoms, an alkoxy group having 1 to 6 carbon atoms or a phenyl group; and p represents an integer of 1 to 3); and $R^4$ and $R^5$ each independently represent an alkyl group having 1 to 6 carbon atoms, an alkenyl group having 2 to 6 carbon atoms, an alkoxy group having 1 to 6 carbon atoms, a phenyl group or a —$O$—$SiR^6R^7R^8$ group (wherein $R^6$, $R^7$ and $R^8$ each independently represent an alkyl group having 1 to 6 carbon atoms, an alkenyl group having 2 to 6 carbon atoms, an alkoxy group having 1 to 6 carbon atoms or a phenyl group):

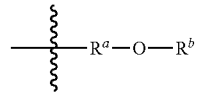
(3-1)

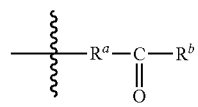
(3-2)

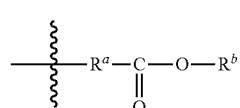
(3-3)

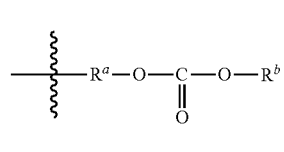
(3-4)

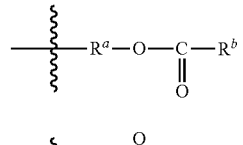
(3-5)

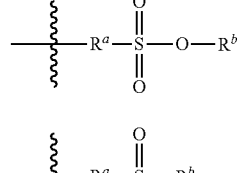
(3-6)

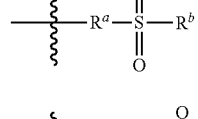
(3-7)

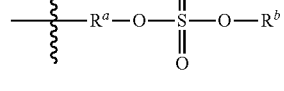
(3-8)

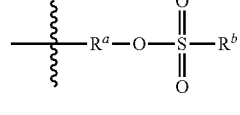
(3-9)

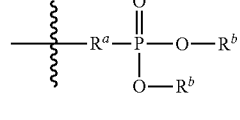
(3-10)

wherein, in Formulae (3-1) to (3-10), $R^a$ represents a divalent hydrocarbon group having 1 to 12 carbon atoms which may be substituted with a halogen atom; and $R^b$ represents a hydrocarbon group having 1 to 12 carbon atoms which may be substituted with a halogen atom, or a —$SiR^{21}R^{22}R^{23}$ group (wherein $R^{21}$, $R^{22}$ and $R^{23}$ each independently represent an alkyl group having 1 to 6 carbon atoms, an alkenyl group having 2 to 6 carbon atoms, an alkoxy group having 1 to 6 carbon atoms or a phenyl group).

<3> The non-aqueous electrolyte solution according to <2>, wherein m is 0 and n is 2 in the Formula (1).

<4> The non-aqueous electrolyte solution according to <3>, wherein, in the Formula (1), $R^1$ is an alkyl group having 1 to 6 carbon atoms, a fluoroalkyl group having 1 to 6 carbon atoms, an aryl group having 6 to 14 carbon atoms (which may be substituted with a fluorine atom, an alkyl group having 1 to 6 carbon atoms or a fluoroalkyl group having 1 to 6 carbon atoms), an alkenyl group having 2 to 6 carbon atoms, an alkyl group having 1 to 6 carbon atoms, which is substituted with one —$SiR^{18}R^{19}R^{20}$ group (wherein $R^{18}$, $R^{19}$ and $R^{20}$ each independently represent an alkyl group having 1 to 6 carbon atoms, an alkenyl group having 2 to 6 carbon atoms, an alkoxy group having 1 to 6 carbon atoms or a phenyl group), a fluoroalkyl group having 1 to 6 carbon atoms, which is substituted with one —$SiR^{18}R^{19}R^{20}$ group (wherein $R^{18}$, $R^{19}$ and $R^{20}$ each independently represent an alkyl group having 1 to 6 carbon atoms, an alkenyl group having 2 to 6 carbon atoms, an alkoxy group having 1 to 6 carbon atoms or a phenyl group), a 5- or 6-membered heterocyclic group (wherein the heterocyclic group is a furyl group, a thienyl group, a pyrrolyl group, an oxazolyl group, an isoxazolyl group, a thiazolyl group, an isothiazolyl group, an imidazolyl group, a pyrazolyl group, a triazolyl group, a tetrazolyl group, a pyridyl group, a pyrimidinyl group, a pyrazinyl group, a pyridazinyl group or a triazinyl group and may be substituted with a fluorine atom, an alkyl group having 1 to 6 carbon atoms or a fluoroalkyl group having 1 to 6 carbon atoms), or a group represented by any one of the Formulae (3-1), (3-9) and (3-10), with the proviso that, in the Formulae (3-1), (3-9) and (3-10), $R^a$ is an alkylene group having 1 to 6 carbon atoms, a fluoroalkylene group having 1 to 6 carbon atoms, a phenylene group (which may be substituted with a fluorine atom, an alkyl group having 1 to 6 carbon atoms or a fluoroalkyl group having 1 to 6 carbon atoms) or an alkenylene group having 2 to 6 carbon atoms, and $R^b$ is an alkyl group having 1 to 6 carbon atoms, a fluoroalkyl group having 1 to 6 carbon atoms, a phenyl group (which may be substituted with a fluorine atom, an alkyl group having 1 to 6 carbon atoms or a fluoroalkyl group having 1 to 6 carbon atoms), an alkenyl group having 2 to 6 carbon atoms, or a —$SiR^{21}R^{22}R^{23}$ group (wherein $R^{21}$, $R^{22}$ and $R^{23}$ are each independently an alkyl group having 1 to 6 carbon atoms, an alkenyl group having 2 to 6 carbon atoms, an alkoxy group having 1 to 6 carbon atoms or a phenyl group).

In the non-aqueous electrolyte solution according to <3> or <4>, it is particularly preferred that $R^1$ be a methyl group, an ethyl group, a linear or branched propyl group, a linear or branched butyl group, a fluoromethyl group, a difluoromethyl group, a trifluoromethyl group, a perfluoroethyl group, a phenyl group (which may be substituted with a fluorine atom, a methyl group, an ethyl group, a propyl group, a butyl group or a trifluoromethyl group), a vinyl group, a propenyl group, an allyl group, a methyl group which is substituted with one —$SiR^{18}R^{19}R^{20}$ group (wherein $R^{18}$, $R^{19}$ and $R^{20}$ are each independently a methyl group, an ethyl group, a linear or branched propyl group, a linear or branched butyl group, a vinyl group, an allyl group or a phenyl group), a fluoromethyl group which is substituted with one —$SiR^{18}R^{19}R^{20}$ group (wherein $R^{18}$, $R^{19}$ and $R^{20}$ are each independently a methyl group, an ethyl group, a linear or branched propyl group, a linear or branched butyl group, a vinyl group, an allyl group or a phenyl group), a difluoromethyl group which is substituted with one group (wherein $R^{18}$, $R^{19}$ and $R^{20}$ are each independently a methyl group, an ethyl group, a linear or branched propyl group, a linear or branched butyl group, a vinyl group, an allyl group or a phenyl group), a thienyl group (which may be substituted with a fluorine atom, an alkyl group having 1 to 6 carbon atoms or a fluoroalkyl group having 1 to 6 carbon atoms), a pyridyl group (which may be substituted with a fluorine atom, an alkyl group having 1 to 6 carbon atoms or a fluoroalkyl group having 1 to 6 carbon atoms), or a group represented by any one of the Formulae (3-1), (3-9) and (3-10), with the proviso that, in the Formulae (3-1), (3-9) and (3-10), $R^a$ is a methylene group, an ethylene group, a propylene group, a butylene group, a fluoromethylene group, a difluoromethylene group, a perfluoroethylene group or a phenylene group (which may be substituted with a fluorine atom, a methyl group, an ethyl group, a propyl group, a butyl group or a trifluoromethyl group), and $R^b$ is a methyl group, an ethyl group, a propyl group, a butyl group, a trifluoromethyl group, a perfluoroethyl group, a phenyl group (which may be substituted with a fluorine atom, a methyl group, an ethyl group, a propyl group, a butyl group or a fluoromethyl group), a vinyl group, a propenyl group, or a —$SiR^{21}R^{22}R^{23}$ group (wherein $R^{21}$, $R^{22}$ and $R^{23}$ are each independently a methyl group, an ethyl group, a linear or branched propyl group, a linear or branched butyl group, a vinyl group, a propenyl group, an allyl group, a methoxy group, an ethoxy group or a phenyl group).

<5> The non-aqueous electrolyte solution according to <3> or <4>, wherein, in the Formula (1), $R^1$ is an alkyl group having 1 to 6 carbon atoms, a fluoroalkyl group having 1 to 6 carbon atoms, an aryl group having 6 to 14 carbon atoms (which may be substituted with a fluorine atom, an alkyl group having 1 to 6 carbon atoms or a fluoroalkyl group having 1 to 6 carbon atoms), an alkenyl group having 2 to 6 carbon atoms, an alkyl group having 1 to 6 carbon atoms, which is substituted with one —$SiR^{18}R^{19}R^{20}$ group (wherein $R^{18}$, $R^{19}$ and $R^{20}$ are each independently an alkyl group having 1 to 6 carbon atoms), a fluoroalkyl group having 1 to 6 carbon atoms which is substituted with one —$SiR^{18}R^{19}R^{20}$ group (wherein $R^{18}$, $R^{19}$ and $R^{20}$ are each independently an alkyl group having 1 to 6 carbon atoms), or a group represented by any one of the Formulae (3-1), (3-9) and (3-10), with the proviso that, in the Formulae (3-1), (3-9) and (3-10), $R^a$ is an alkylene group having 1 to 6 carbon atoms and $R^b$ is an alkyl group having 1 to 6 carbon atoms or a —$SiR^{21}R^{22}R^{23}$ group (wherein $R^{21}$, $R^{22}$ and $R^{23}$ are each independently an alkyl group having 1 to 6 carbon atoms); and $R^3$, $R^4$ and $R^5$ are each independently an alkyl group having 1 to 6 carbon atoms, an alkenyl group having 2 to 6 carbon atoms or a phenyl group.

<6> The non-aqueous electrolyte solution according to any one of <3> to <5>, wherein the compound represented by the Formula (1) is methylphosphonic acid bis(trimethylsilyl) ester, methylphosphonic acid bis(tert-butyldimethylsilyl) ester, methylphosphonic acid bis(allyldimethylsilyl) ester, methylphosphonic acid bis(triphenylsilyl) ester, phenylphosphonic acid bis(trimethylsilyl) ester, vinylphosphonic acid bis(trimethylsilyl) ester, 1-propenylphosphonic acid bis(trimethylsilyl) ester, [difluoro(trimethylsilyl)methyl]phosphonic acid bis(trimethylsilyl) ester, [(trimethylsilyloxy)methyl]phosphonic acid bis(trimethylsilyl) ester, [(methanesulfonyloxy)methyl]phosphonic acid bis(trimethylsilyl) ester, methylenebisphosphonic acid tetrakis(trimethylsilyl) ester, or 2,4,4,6,6-pentamethyl-1,3,5-trioxa-2-phospha-4,6-disilacyclohexane-2-oxide.

<7> The non-aqueous electrolyte solution according to any one of <1> to <6>, wherein the content of the silyl ester group-containing phosphonic acid derivative is 0.001% by mass to 10% by mass.

<8> The non-aqueous electrolyte solution according to any one of <1> to <7>, further comprising a tetrafluoroborate.

<9> The non-aqueous electrolyte solution according to <8>, wherein the tetrafluoroborate is lithium tetrafluoroborate ($LiBF_4$).

<10> The non-aqueous electrolyte solution according to claim <8> or <9>, wherein the concentration of the tetrafluoroborate is 0.0001 mol/L to 2 mol/L.

<11> An additive for lithium secondary batteries, comprising a compound represented by the following Formula (1):

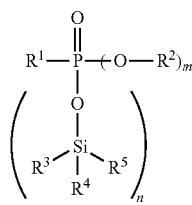

(1)

wherein, in the Formula(1), m represents 0 or 1; n represents 1 or 2; m+n=2;

$R^1$ represents
a hydrogen atom,
an alkyl group having 1 to 12 carbon atoms,
a haloalkyl group having 1 to 12 carbon atoms,
an aryl group having 6 to 14 carbon atoms (which may be substituted with a halogen atom, an alkyl group having 1 to 6 carbon atoms or a haloalkyl group having 1 to 6 carbon atoms),
an alkenyl group having 2 to 12 carbon atoms,
an alkyl group having 1 to 6 carbon atoms, which is substituted with at least one $-SiR^{18}R^{19}R^{20}$ group (wherein $R^{18}$, $R^{19}$ and $R^{20}$ each independently represent an alkyl group having 1 to 6 carbon atoms, an alkenyl group having 2 to 6 carbon atoms, an alkoxy group having 1 to 6 carbon atoms or a phenyl group),
a haloalkyl group having 1 to 6 carbon atoms, which is substituted with at least one $-SiR^{18}R^{19}R^{20}$ group (wherein $R^{18}$, $R^{19}$ and $R^{20}$ each independently represent an alkyl group having 1 to 6 carbon atoms, an alkenyl group having 2 to 6 carbon atoms, an alkoxy group having 1 to 6 carbon atoms or a phenyl group),
a 5- or 6-membered heterocyclic group (which may or may not be substituted), or
a group represented by any one of the following Formulae (3-1) to (3-10);

$R^2$ represents
a hydrogen atom,
an alkyl group having 1 to 6 carbon atoms,
a haloalkyl group having 1 to 6 carbon atoms,
an alkenyl group having 2 to 6 carbon atoms, or
a phenyl group (which may be substituted with a halogen atom, an alkyl group having 1 to 6 carbon atoms or a haloalkyl group having 1 to 6 carbon atoms);

$R^3$ represents
an alkyl group having 1 to 6 carbon atoms,
an alkenyl group having 2 to 6 carbon atoms,
an alkoxy group having 1 to 6 carbon atoms,
a phenyl group,
a $-O-SiR^6R^7R^8$ group (wherein $R^6$, $R^7$ and $R^8$ each independently represent an alkyl group having 1 to 6 carbon atoms, an alkenyl group having 2 to 6 carbon atoms, an alkoxy group having 1 to 6 carbon atoms or a phenyl group), or
a group in which, when n is 2, two $R^3$s are linked with each other to form $-O-$, an alkylene group having 1 to 3 carbon atoms or $-O-(SiR^{16}R^{17}-O)_p-$ (wherein $R^{16}$ and $R^{17}$ independently represent an alkyl group having 1 to 6 carbon atoms, an alkenyl group having 2 to 6 carbon atoms, an alkoxy group having 1 to 6 carbon atoms or a phenyl group; and p represents an integer of 1 to 3); and $R^4$ and $R^5$ each independently represent
an alkyl group having 1 to 6 carbon atoms, an alkenyl group having 2 to 6 carbon atoms, an alkoxy group having 1 to 6 carbon atoms, a phenyl group or a $-O-SiR^6R^7R^8$ group (wherein $R^6$, $R^7$ and $R^8$ each independently represent an alkyl group having 1 to 6 carbon atoms, an alkenyl group having 2 to 6 carbon atoms, an alkoxy group having 1 to 6 carbon atoms or a phenyl group):

(3-1)

(3-2)

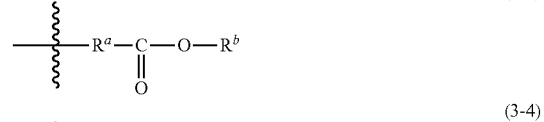

(3-3)

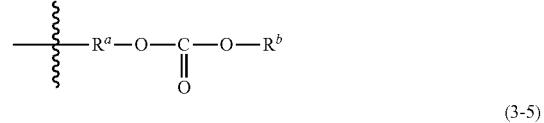

(3-4)

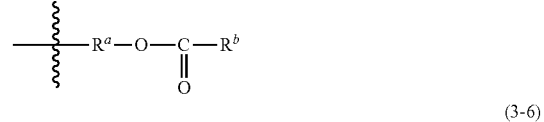

(3-5)

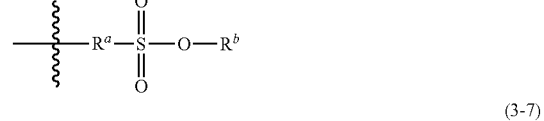

(3-6)

(3-7)

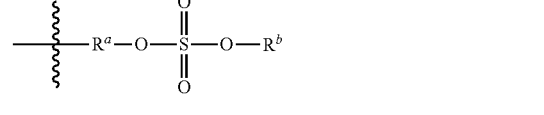

(3-8)

9

-continued

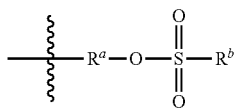
(3-9)

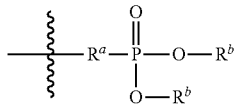
(3-10)

wherein, in Formulae (3-1) to (3-10), $R^a$ represents a divalent hydrocarbon group having 1 to 12 carbon atoms which may be substituted with a halogen atom; and $R^b$ represents a hydrocarbon group having 1 to 12 carbon atoms which may be substituted with a halogen atom, or a —$SiR^{21}R^{22}R^{23}$ group (wherein $R^{21}$, $R^{22}$ and $R^{23}$ each independently represent an alkyl group having 1 to 6 carbon atoms, an alkenyl group having 2 to 6 carbon atoms, an alkoxy group having 1 to 6 carbon atoms or a phenyl group).

<12> A lithium secondary battery, comprising:
a positive electrode;
a negative electrode containing, as a negative electrode active material, at least one selected from lithium metal, lithium-containing alloys, metals or alloys that are capable of forming an alloy with lithium, oxides capable of doping/dedoping lithium ions, transition metal nitrides capable of doping/dedoping lithium ions and carbon materials capable of doping/dedoping lithium ions; and
the non-aqueous electrolyte solution according to any one of <1> to <10>.

<13> A lithium secondary battery, which is obtained by charging/discharging a lithium secondary battery comprising:
a positive electrode;
a negative electrode containing, as a negative electrode active material, at least one selected from lithium metal, lithium-containing alloys, metals or alloys that are capable of forming an alloy with lithium, oxides capable of doping/dedoping lithium ions, transition metal nitrides capable of doping/dedoping lithium ions and carbon materials capable of doping/dedoping lithium ions; and
the non-aqueous electrolyte solution according to any one of <1> to <10>.

Advantageous Effects of Invention

According to the present invention, a non-aqueous electrolyte solution which can improve the output characteristics of a battery by reducing the battery resistance, and inhibit deterioration of performance in a high-temperature environment; a lithium secondary battery utilizing the non-aqueous electrolyte solution; and an additive for lithium secondary batteries which is useful for the non-aqueous electrolyte solution can be provided.

BRIEF DESCRIPTION OF DRAWINGS

FIG. 1 is a schematic cross-sectional view of a coin-type battery showing one example of the lithium secondary battery according to the present invention.

DESCRIPTION OF EMBODIMENTS

Hereinafter, the non-aqueous electrolyte solution, the lithium secondary battery and the additive for lithium secondary batteries according to the present invention will be described in detail.

10

<Non-Aqueous Electrolyte Solution>

The non-aqueous electrolyte solution of the present invention contains a silyl ester group-containing phosphonic acid derivative as an additive.

When used as a non-aqueous electrolyte solution of a battery (for example, a lithium secondary battery), the non-aqueous electrolyte solution of the present invention reduces the battery resistance and improves the storage properties of the battery in a high-temperature environment. Therefore, by using the non-aqueous electrolyte solution of the present invention, an extended battery service life can be realized.

(Silyl Ester Group-Containing Phosphonic Acid Derivative)

The phosphonic acid derivative containing a silyl ester group in the present invention (hereinafter, also referred to as "silyl ester group-containing phosphonic acid derivative") is not particularly restricted; however, from the viewpoint of attaining the effects of the present invention more effectively (particularly, from the viewpoint of further improving the battery storage properties in a high-temperature environment), the silyl ester group-containing phosphonic acid derivative is preferably a compound represented by the following Formula (1).

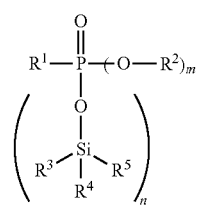
(1)

In the Formula (1), m represents 0 to 1, n represents 1 or 2, and m+n=2;

$R^1$ represents a hydrogen atom or a monovalent organic group having 1 to 36 carbon atoms.

$R^2$ represents a hydrogen atom, an alkyl group having 1 to 6 carbon atoms, a haloalkyl group having 1 to 6 carbon atoms, an alkenyl group having 2 to 6 carbon atoms or a phenyl group (which may be substituted with a halogen atom, an alkyl group having 1 to 6 carbon atoms or a haloalkyl group having 1 to 6 carbon atoms).

$R^3$ represents an alkyl group having 1 to 6 carbon atoms, an alkenyl group having 2 to 6 carbon atoms, an alkoxy group having 1 to 6 carbon atoms, a phenyl group, a —O—$SiR^6R^7R^8$ group (wherein $R^6$, $R^7$ and $R^8$ each independently represent an alkyl group having 1 to 6 carbon atoms, an alkenyl group having 2 to 6 carbon atoms, an alkoxy group having 1 to 6 carbon atoms or a phenyl group) or a group in which, when n is 2, two $R^3$s are linked with each other to form —O—, an alkylene group having 1 to 3 carbon atoms or —O—$(SiR^{16}R^{17}$—$O)_p$— (wherein $R^{16}$ and $R^{17}$ independently represent an alkyl group having 1 to 6 carbon atoms, an alkenyl group having 2 to 6 carbon atoms, an alkoxy group having 1 to 6 carbon atoms or a phenyl group; and p represents an integer of 1 to 3).

That is, when the above-described n is 2, (1) two $R^3$s may each independently be an alkyl group having 1 to 6 carbon atoms, an alkenyl group having 2 to 6 carbon atoms, an alkoxy group having 1 to 6 carbon atoms, a phenyl group or the above-described —O—$SiR^6R^7R^8$ group, or (2) two $R^3$s may be linked with each other to become —O—, an alkylene group having 1 to 3 carbon atoms or the above-described —O—(SiR$^{16}$R$^{17}$—O)$_p$—, thereby forming a ring containing a P atom, an O atom and a Si atom.

R$^4$ and R$^5$ each independently represent an alkyl group having 1 to 6 carbon atoms, an alkenyl group having 2 to 6 carbon atoms, an alkoxy group having 1 to 6 carbon atoms, a phenyl group or a —O—SiR$^6$R$^7$R$^8$ group (wherein R$^6$, R$^7$ and R$^8$ each independently represent an alkyl group having 1 to 6 carbon atoms, an alkenyl group having 2 to 6 carbon atoms, an alkoxy group having 1 to 6 carbon atoms or a phenyl group).

Among the compounds represented by the Formula (1), a compound in which n is 2 and "two R$^3$s are linked with each other to form —O—, an alkylene group having 1 to 3 carbon atoms or —O—(SiR$^{16}$R$^{17}$—O)$_p$— (wherein R$^{16}$ and R$^{17}$ independently represent an alkyl group having 1 to 6 carbon atoms, an alkenyl group having 2 to 6 carbon atoms, an alkoxy group having 1 to 6 carbon atoms or a phenyl group; and p represents an integer of 1 to 3)" is represented by the following Formula (2).

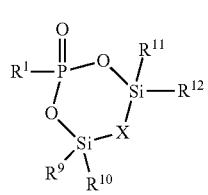

(2)

In the Formula (2),
R$^1$ has the same definitions as R$^1$ in the Formula (1);
R$^9$, R$^{10}$, R$^{11}$ and R$^{12}$ each independently represent
an alkyl group having 1 to 6 carbon atoms,
an alkenyl group having 2 to 6 carbon atoms,
an alkoxy group having 1 to 6 carbon atoms,
a phenyl group, or
a —O—SiR$^{13}$R$^{14}$R$^{15}$ group (wherein R$^{13}$, R$^{14}$ and R$^{15}$ each independently represent an alkyl group having 1 to 6 carbon atoms, an alkenyl group having 2 to 6 carbon atoms, an alkoxy group having 1 to 6 carbon atoms or a phenyl group); and
X represents
an oxygen atom,
an alkylene group having 1 to 3 carbon atoms, or
a —O—(SiR$^{16}$R$^{17}$—O)$_p$— group (wherein R$^{16}$ and R$^{17}$ each independently represent an alkyl group having 1 to 6 carbon atoms, an alkenyl group having 2 to 6 carbon atoms, an alkoxy group having 1 to 6 carbon atoms or a phenyl group; and p represents an integer of 1 to 3).

In R$^1$ of the Formula (1) (including the case of the Formula (2); the same applies hereinafter), as the "monovalent organic group having 1 to 36 carbon atoms", a group having C, H, O, N, P, S, Si and a halogen element as constituent elements is preferred.

The above-described R$^1$ is more preferably
a hydrogen atom,
an alkyl group having 1 to 12 carbon atoms,
a haloalkyl group having 1 to 12 carbon atoms,
an aryl group having 6 to 14 carbon atoms (which may be substituted with a halogen atom, an alkyl group having 1 to 6 carbon atoms or a haloalkyl group having 1 to 6 carbon atoms),
an alkenyl group having 2 to 12 carbon atoms,
an alkyl group having 1 to 6 carbon atoms, which is substituted with at least one —SiR$^{18}$R$^{19}$R$^{20}$ group (wherein R$^{18}$, R$^{19}$ and R$^{20}$ each independently represent an alkyl group having 1 to 6 carbon atoms, an alkenyl group having 2 to 6 carbon atoms, an alkoxy group having 1 to 6 carbon atoms or a phenyl group),
a haloalkyl group having 1 to 6 carbon atoms, which is substituted with at least one —SiR$^{18}$R$^{19}$R$^{20}$ group (wherein R$^{18}$, R$^{19}$ and R$^{20}$ each independently represent an alkyl group having 1 to 6 carbon atoms, an alkenyl group having 2 to 6 carbon atoms, an alkoxy group having 1 to 6 carbon atoms or a phenyl group),
a 5- or 6-membered heterocyclic group (which may or may not be substituted), or
a group represented by any one of the later-described Formula (3-1) to (3-10).

In R$^1$ of the Formula (1), examples of the "an alkyl group having 1 to 12 carbon atoms" include methyl group, ethyl group, n-propyl group, isopropyl group, n-butyl group, isobutyl group, sec-butyl group, tert-butyl group, pentyl group, 2-methylbutyl group, 1-methylpentyl group, neopentyl group, 1-ethylpropyl group, hexyl group, 3,3-dimethylbutyl group, heptyl group, octyl group, nonyl group, undecanyl group and dodecanyl group.

In R$^1$ of the Formula (1), examples of the "haloalkyl group having 1 to 12 carbon atoms" include fluoromethyl group, difluoromethyl group, trifluoromethyl group, 2,2,2-trifluoroethyl group, perfluoroethyl group, perfluoropropyl group, perfluorobutyl group, perfluoropentyl group, perfluorohexyl group, perfluoroheptyl group, perfluorooctyl group, perfluorononyl group, perfluorodecyl group, perfluoroundecanyl group, perfluorododecanyl group, perfluoroisopropyl group, perfluoroisobutyl group, chloromethyl group, chloroethyl group, chloropropyl group, bromomethyl group, bromoethyl group, bromopropyl group, iodomethyl group, iodoethyl group and iodopropyl group.

In R$^1$ of the Formula (1), examples of the "aryl group having 6 to 14 carbon atoms (which may be substituted with a halogen atom, an alkyl group having 1 to 6 carbon atoms or a haloalkyl group having 1 to 6 carbon atoms)" include phenyl group, methylphenyl group, dimethylphenyl group, trimethylphenyl group, tetramethylphenyl group, ethylphenyl group, n-propylphenyl group, isopropylphenyl group, butylphenyl group, isobutylphenyl group, sec-butylphenyl group, tert-butylphenyl group, pentylphenyl group, hexylphenyl group, fluorophenyl group, difluorophenyl group, trifluorophenyl group, tetrafluorophenyl group, pentafluorophenyl group, chlorophenyl group, bromophenyl group, naphthyl group, methylnaphthyl group, ethylnaphthyl group and anthryl group.

In R$^1$ of the Formula (1), examples of the "alkenyl group having 2 to 12 carbon atoms" include vinyl group, 1-propenyl group, allyl group, butenyl group, butene-3-yl group, pentenyl group, pentene-4-yl group, hexenyl group, hexene-5-yl group, heptenyl group, octenyl group, nonenyl group, decenyl group, undecenyl group and dodecenyl group.

In R$^1$ of the Formula (1), examples of the "alkyl group having 1 to 6 carbon atoms, which is substituted with at least one —SiR$^{18}$R$^{19}$R$^{20}$ group (wherein R$^{18}$, R$^{19}$ and R$^{20}$ each independently represent an alkyl group having 1 to 6 carbon atoms, an alkenyl group having 2 to 6 carbon atoms, an alkoxy group having 1 to 6 carbon atoms or a phenyl group)" or the "haloalkyl group having 1 to 6 carbon atoms, which is substituted with at least one —SiR$^{18}$R$^{19}$R$^{20}$ group (wherein R$^{18}$, R$^{19}$ and R$^{20}$ each independently represent an alkyl group having 1 to 6 carbon atoms, an alkenyl group having 2 to 6 carbon atoms, an alkoxy group having 1 to 6 carbon atoms or a phenyl group)" include (trimethylsilyl)methyl group, (triethylsilyl)methyl group, (tri-n-propylsilyl)methyl group, (tri-isopropylsilyl)methyl group, (tri-n-butylsilyl)methyl group, (triisobutylsilyl)methyl group, (tri-sec-butylsilyl)methyl group, (tri-tert-butylsilyl)methyl group, (tripentylsilyl)methyl group, (trihexylsilyl)methyl group, (triphenylsilyl)methyl group, (tert-butyl dimethylsilyl)methyl group, (dimethylphenylsilyl)methyl group, (methyl diphenyl silyl)methyl group, (ethyldimethylsilyl)methyl group, (dimethylpropylsilyl)methyl group, (tort-butyldimethylsilyl)methyl group, (hexyldimethylsilyl)methyl group, (dimethylphenylsilyl)methyl group, (methyldiphenylsilyl)methyl group, (dimethylvinylsilyl)methyl group, (allyldimethylsilyl)methyl group, (dimethyl-1-propenylsilyl)methyl group, (butenyldimethylsilyl)methyl group, (dimethylpentenylsilyl)methyl group, (hexenyldimethylsilyl)methyl group, (methoxydimethylsilyl)methyl group, (ethoxydimethylsilyl)methyl group, (butoxydimethylsilyl)methyl group, (dimethylphenoxysilyl)methyl group, (diethoxymethylsilyl)methyl group, (methyldiphenoxysilyl)methyl group, (trimethylsilyefluoromethyl group, (trimethylsilyl)difluoromethyl group, (trimethylsilyl)chloromethyl group, (trimethylsilyl)dichloromethyl group, (trimethylsilyl)bromomethyl group, (trimethylsilyl)dibromomethyl group, (trimethylsilyl)perfluoroethyl group, (trimethylsilyl)perfluoropropyl group, (trimethylsilyl)perfluorobutyl group, (trimethylsilyl)perfluoropentyl group, (trimethylsilyl)perfluorohexyl group, (triphenylsilyl)difluoromethyl group and (trimethoxysilyl)difluoromethyl group.

In $R^1$ of the Formula (1), examples of the "5- or 6-membered heterocyclic group (which may or may not be substituted)" include heterocyclic groups containing an oxygen atom, a nitrogen atom and a sulfur atom as constituent elements. Specific examples thereof include furyl group, thienyl group, pyrrolyl group, oxazolyl group, isoxazolyl group, thiazolyl group, isothiazolyl group, imidazolyl group, pyrazolyl group, triazolyl group, tetrazolyl group, pyridyl group, pyrimidinyl group, pyrazinyl group, pyridazinyl group and triazinyl group.

Furthermore, it is also preferred that $R^1$ in the Formula (1) be a group represented by any one of the following Formulae (3-1) to (3-10).

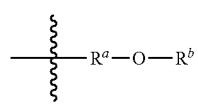

(3-1)

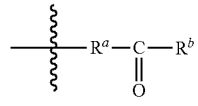

(3-2)

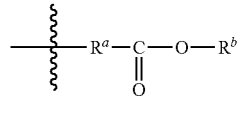

(3-3)

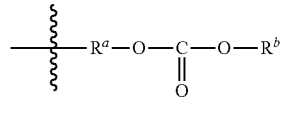

(3-4)

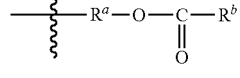

(3-5)

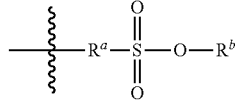

(3-6)

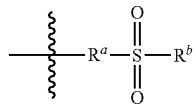

(3-7)

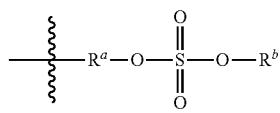

(3-8)

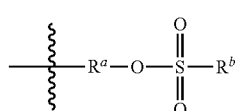

(3-9)

(3-10)

In the Formulae (3-1) to (3-10), $R^a$ represents a divalent hydrocarbon group having 1 to 12 carbon atoms which may be substituted with a halogen atom. $R^b$ represents a hydrocarbon group having 1 to 12 carbon atoms which may be substituted with a halogen atom, or a $-SiR^{21}R^{22}R^{23}$ group (wherein $R^{21}$, $R^{22}$ and $R^{23}$ each independently represent an alkyl group having 1 to 6 carbon atoms, an alkenyl group having 2 to 6 carbon atoms, an alkoxy group having 1 to 6 carbon atoms or a phenyl group).

In $R^a$ of the Formulae (3-1) to (3-10), examples of the "divalent hydrocarbon group having 1 to 12 carbon atoms which may be substituted with a halogen atom" include alkylene groups having 1 to 12 carbon atoms, haloalkylene groups having 1 to 12 carbon atoms, alkenylene groups having 1 to 12 carbon atoms and phenylene groups (which may be substituted with a halogen atom, an alkyl group having 1 to 6 carbon atoms or a haloalkyl group having 1 to 6 carbon atoms).

More specific examples include methylene group, ethylene group, propylene group, butylene group, pentylene group, 2-methylbutylene group, 1-methylpentylene group, neopentylene group, 1-ethylpropylene group, hexylene group, 3,3-dimethylbutylene group, heptylene group, octylene group, nonylene group, undecanylene group, dodecanylene group, fluoromethylene group, difluoromethylene group, fluoroethylene group, 1,2-difluoroethylene group, trifluoroethylene group, perfluoroethylene group, perfluoropropylene group, perfluorobutylene group, perfluoropentylene group, perfluorohexylene group, perfluoroheptylene group, perfluorooctylene group, perfluorononylene group, perfluorodecylene group, perfluoroundecanylene group, perfluorododecanylene group, perfluoroisopropylene group, perfluoroisobutylene group, chloromethylene group, chloroethylene group, chloropropylene group, bromomethylene group, bromoethylene group, bromopropylene group, iodomethylene group, iodoethylene group, iodopropylene group, vinylene group, 1-propenylene group, allylene group, butenylene group, butene-3-ylene group, pentenylene group, pentene-4-ylene group, hexenylene group, hexene-5-ylene group, heptenylene group, octenylene group, nonenylene group, decenylene group, undecenylene group, dodecenylene group, phenylene group, methylphenylene group, ethylphenylene group, propylphenylene group, butylphenylene group, hexylphenylene group, fluorophenylene group, chlorophenylene group, bromophenylene group, iodophenylene group, (fluoromethyl)phenylene group, (difluoromethyl)phenylene group and (trifluoromethyl)phenylene group.

In $R^b$ of the Formulae (3-1) to (3-10), examples of the "hydrocarbon group having 1 to 12 carbon atoms which may be substituted with a halogen atom" include alkyl groups having 1 to 12 carbon atoms, haloalkyl groups having 1 to 12 carbon atoms, alkenyl groups having 1 to 12 carbon atoms and phenyl groups (which may be substituted with a halogen atom, an alkyl group having 1 to 6 carbon atoms or a haloalkyl group having 1 to 6 carbon atoms).

More specific examples include methyl group, ethyl group, n-propyl group, isopropyl group, n-butyl group, isobutyl group, sec-butyl group, tert-butyl group, pentyl group, 2-methylbutyl group, 1-methylpentyl group, neopentyl group, 1-ethylpropyl group, hexyl group, 3,3-dimethylbutyl group, heptyl group, octyl group, nonyl group, undecanyl group, dodecanyl group, fluoromethyl group, difluoromethyl group, trifluoromethyl group, 2,2,2-trifluoroethyl group, perfluoroethyl group, perfluoropropyl group, perfluorobutyl group, perfluoropentyl group, perfluorohexyl group, perfluoroheptyl group, perfluorooctyl group, perfluorononyl group, perfluorodecyl group, perfluoroundecanyl group, perfluorododecanyl group, perfluoroisopropyl group, perfluoroisobutyl group, chloromethyl group, chloroethyl group, chioropropyl group, bromomethyl group, bromoethylgroup, bromopropyl group, iodomethyl group, iodoethyl group, iodopropyl group, vinyl group, 1-propenyl group, allyl group, butenyl group, butene-3-yl group, pentenyl group, pentene-4-yl group, hexenyl group, hexene-5-yl group, heptenyl group, octenyl group, nonenyl group, decenyl group, undecenyl group, dodecenyl group, phenyl group, methylphenyl group, dimethylphenyl group, trimethylphenyl group, tetramethylphenyl group, ethylphenyl group, n-propylphenyl group, isopropylphenyl group, butylphenyl group, isobutylphenyl group, sec-butylphenyl group, tert-butylphenyl group, pentylphenyl group, hexylphenyl group, fluorophenyl group, difluorophenyl group, trifluorophenyl group, tetrafluorophenyl group, pentafluorophenyl group, chlorophenyl group and bromophenyl group.

In $R^b$ of the Formulae (3-1) to (3-10), examples of the "—$SiR^{21}R^{22}R^{23}$ group (wherein $R^{21}$, $R^{22}$ and $R^{23}$ each independently represent an alkyl group having 1 to 6 carbon atoms, an alkenyl group having 2 to 6 carbon atoms, an alkoxy group having 1 to 6 carbon atoms or a phenyl group)" include trimethylsilyl group, triethylsilyl group, tri-n-propylsilyl group, triisopropylsilyl group, tri-n-butylsilyl group, triisobutylsilyl group, tri-sec-butylsilyl group, tri-tert-butylsilyl group, tripentylsilyl group, trihexylsilyl group, triphenylsilyl group, ethyldimethylsilyl group, dimethylpropylsilyl group, tert-butyldimethylsilyl group, hexyldimethylsilyl group, dimethylphenylsilyl group, methyldiphenylsilyl group, dimethylvinylsilyl group, allyldimethylsilyl group, dimethyl-1-propenylsilyl group, butenyldimethylsilyl group, dimethylpcntenylsilyl group, hexenyldimethylsilyl group, methoxydimethylsilyl group, ethoxydimethylsilyl group, butoxydimethylsilyl group, dimethylphenoxysilyl group, diethoxymethylsilyl group and methyldiphenoxysilyl group.

In $R^2$ of the Formula (1), examples of the "alkyl group having 1 to 6 carbon atoms" include methyl group, ethyl group, n-propyl group, isopropyl group, n-butyl group, isobutyl group, sec-butyl group, tert-butyl group, pentyl group, 2-methylbutyl group, 1-methylpentyl group, neopentyl group, 1-ethylpropyl group, hexyl group and 3,3-dimethylbutyl group.

In $R^2$ of the Formula (1), examples of the "haloalkyl group having 1 to 6 carbon atoms" include fluoromethyl group, difluoromethyl group, trifluoromethyl group, 2,2,2-trifluoroethyl group, perfluoroethyl group, perfluoropropyl group, perfluorobutyl group, perfluoropentyl group, perfluorohexyl group, perfluoroisopropyl group, perfluoroisobutyl group, chloromethyl group, chloroethyl group, chloropropyl group, bromomethyl group, bromoethyl group, bromopropyl group, iodomethyl group, iodoethyl group and iodopropyl group.

In $R^2$ of the Formula (1), examples of the "alkenyl group having 2 to 6 carbon atoms" include vinyl group, 1-propenyl group, allyl group, butenyl group, butene-3-yl group, pentenyl group, pentene-4-yl group, hexenyl group and hexene-5-yl group.

In $R^2$ of the Formula (1), examples of the "phenyl group (which may be substituted with a halogen atom, an alkyl group having 1 to 6 carbon atoms or a haloalkyl group having 1 to 6 carbon atoms)" include phenyl group, methylphenyl group, dimethylphenyl group, trimethylphenyl group, tetramethylphenyl group, pentamethylphenyl group, ethylphenyl group, n-propylphenyl group, isopropylphenyl group, butylphenyl group, isobutylphenyl group, sec-butylphenyl group, tert-butylphenyl group, pentylphenyl group, hexylphenyl group, fluorophenyl group, difluorophenyl group, trifluorophenyl group, tetrafluorophenyl group, pentafluorophenyl group, chlorophenyl group, bromophenyl group, (monofluoromethyl)phenyl group, (difluoromethyl)phenyl group and (trifluoromethyl)phenyl group.

In $R^3$, $R^4$ and $R^5$ of the Formula (1), examples of the "alkyl group having 1 to 6 carbon atoms" include methyl group, ethyl group, n-propyl group, isopropyl group, n-butyl group, isobutyl group, sec-butyl group, tert-butyl group, pentyl group, 2-methylbutyl group, 1-methylpentyl group, neopentyl group, 1-ethylpropyl group, hexyl group and 3,3-dimethylbutyl group.

In $R^3$, $R^4$ and $R^5$ of the Formula (1), examples of the "alkenyl group having 2 to 6 carbon atoms" include vinyl group, 1-propenyl group, allyl group, butenyl group, butene-3-yl group, pentenyl group, pentene-4-yl group, hexenyl group and hexene-5-yl group.

In $R^3$, $R^4$ and $R^5$ of the Formula (1), examples of the "alkoxy group having 1 to 6 carbon atoms" include methoxy group, ethoxy group, propyloxy group, isopropyloxy group, butyloxy group, isobutyloxy group, sec-butyloxy group, tert-butyloxy group, pentyloxy group, 2-methylbutyloxy group, 1-methylpentyloxy group, neopentyloxy group, 3,3-dimethylbutyloxy group and hexyloxy group.

In $R^3$, $R^4$ and $R^5$ of the Formula (1), examples of the "—O—$SiR^6R^7R^8$ group (wherein $R^6$, $R^7$ and $R^8$ each independently represent an alkyl group having 1 to 6 carbon atoms, an alkenyl group having 2 to 6 carbon atoms, an alkoxy group having 1 to 6 carbon atoms or a phenyl group)" include trimethylsilyloxy group, triethylsilyloxy group, tri-n-propylsilyloxy group, triisopropylsilyloxy group, tri-n-butylsilyloxy group, triisobutylsilyloxy group, tri-sec-butylsilyloxy group, tri-tert-butylsilyloxy group, tripentylsilyloxy group, trihexylsilyloxy group, triphenylsilyloxy group, ethyldimethylsilyloxy group, dimethylpropylsilyloxy group, tert-butyldimethylsilyloxy group, hexyldimethylsilyloxy group, dimethylphenylsilyloxy group, methyldiphenylsilyloxy group, dimethylvinylsilyloxy group, allyldimethylsilyloxy group, dimethyl-1-propenylsilyloxy group, butenyldimethylsilyloxy group, dimethylpentenylsilyloxy group, hexenyldimethylsilyloxy group, methoxydimethylsilyloxy group, ethoxydimethylsilyloxy group, butoxydimethylsilyloxy group, dimethylphenoxysilyloxy group, diethoxymethylsilyloxy group and methyldiphenoxysilyloxy group.

As for m and n in the Formula (1), there are two types of combinations, which are a combination where m is 0 and n is 2 (hereinafter, also indicated as "<m=0, n=2>") and a combination where m is 1 and n is 1 (hereinafter, also indicated as "<m=1, n=1>").

In $R^9$, $R^{10}$, $R^{11}$ and $R^{12}$ of the Formula (2), examples of "an alkyl group having 1 to 6 carbon atoms, an alkenyl group having 2 to 6 carbon atoms, an alkoxy group having 1 to 6 carbon atoms, a phenyl group or a —O—$SiR^{13}R^{14}R^{15}$ group (wherein $R^{13}$, $R^{14}$ and $R^{15}$ each independently represent an alkyl group having 1 to 6 carbon atoms, an alkenyl group having 2 to 6 carbon atoms, an alkoxy group having 1 to 6 carbon atoms or a phenyl group)" include the same substituents as those exemplified for $R^3$, $R^4$ and $R^5$ of the Formula (1).

In X of the Formula (2), examples of the "alkylene group having 1 to 3 carbon atoms" include methylene group, ethylene group, propylene group and 1-methylethylene group.

In X of the Formula (2), examples of $R^{16}$ and $R^{17}$ in the "—O—($SiR^{16}R^{17}$—O)$_p$— group (wherein $R^{16}$ and $R^{17}$ each independently represent an alkyl group having 1 to 6 carbon atoms, an alkenyl group having 2 to 6 carbon atoms, an alkoxy group having 1 to 6 carbon atoms or a phenyl group; and p represents an integer of 1 to 3)" include methyl group, ethyl group, n-propyl group, isopropyl group, n-butyl group, isobutyl group, sec-butyl group, tert-butyl group, pentyl group, 2-methylbutyl group, 1-methylpentyl group, neopentyl group, 1-ethylpropyl group, hexyl group, 3,3-dimethylbutyl group, methoxy group, ethoxy group, propyloxy group, isopropyloxy group, butyloxy group, isobutyloxy group, sec-butyloxy group, tert-butyloxy group, pentyloxy group, 2-methylbutyloxy group, 1-methylpentyloxy group, neopentyloxy group, 3,3-dimethylbutyloxy group, hexyloxy group and phenyl group.

Specific examples of X are not particularly restricted; however, they include the following Formulae (X-1) to (X-26).

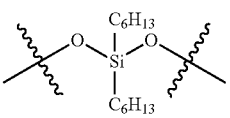
(X-1)

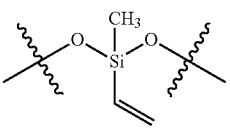
(X-2)

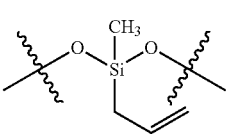
(X-3)

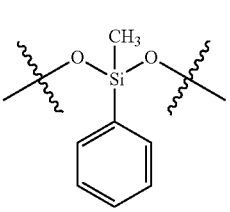
(X-4)

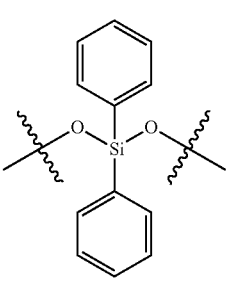
(X-5)

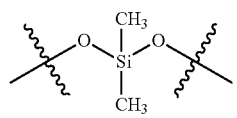
(X-6)

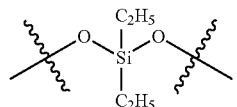
(X-7)

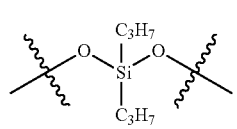
(X-8)

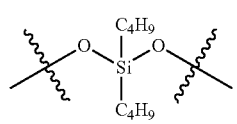
(X-9)

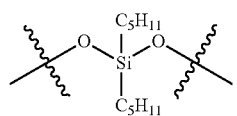
(X-10)

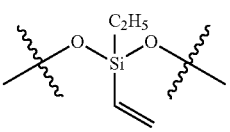
(X-11)

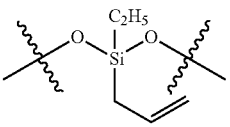
(X-12)

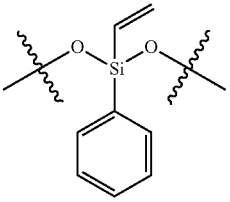
(X-13)

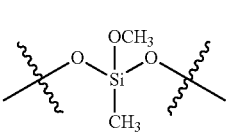
(X-14)

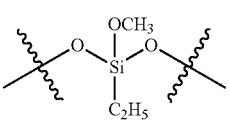
(X-15)

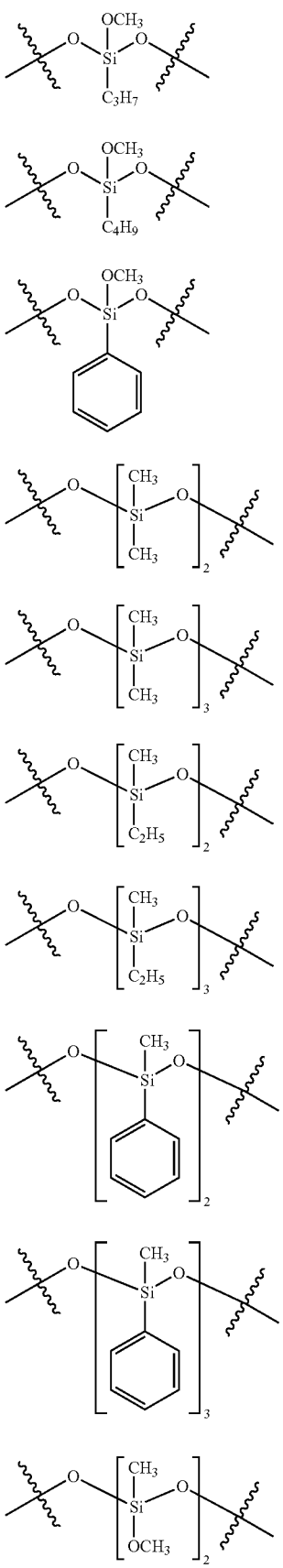

Preferred scope of $R^1$ in the Formulae (1) and (2) will now be described from the viewpoints of enabling to attain an improvement in the battery output characteristics by reducing the battery resistance, and inhibiting deterioration of performance in a high-temperature environment.

As described in the above, an example of $R^1$ "an alkyl group having 1 to 12 carbon atoms"; however, $R^1$ is more preferably an alkyl group having 1 to 6 carbon atoms, particularly preferably a methyl group, an ethyl group, a linear or branched propyl group, or a linear or branched butyl group.

Furthermore, as described in the above, an example of $R^1$ is "a haloalkyl group having 1 to 12 carbon atoms"; however, $R^1$ is more preferably a fluoroalkyl group having 1 to 6 carbon atoms, particularly preferably a fluoromethyl group, a difluoromethyl group, a trifluoromethyl group or a perfluoroethyl group.

Furthermore, as described in the above, an example of $R^1$ is "an aryl group having 6 to 14 carbon atoms (which may be substituted with a halogen atom, an alkyl group having 1 to 6 carbon atoms or a haloalkyl group having 1 to 6 carbon atoms)"; however, $R^1$ is more preferably an aryl group having 6 to 14 carbon atoms (which may be substituted with a fluorine atom, an alkyl group having 1 to 6 carbon atoms or a fluoroalkyl group having 1 to 6 carbon atoms), particularly preferably a phenyl group (which may be substituted with a fluorine atom, a methyl group, an ethyl group, a propyl group, a butyl group or a trifluoromethyl group).

Furthermore, as described in the above, an example of $R^1$ is "an alkenyl group having 2 to 12 carbon atoms"; however, $R^1$ is preferably an alkenyl group having 2 to 6 carbon atoms, more preferably a vinyl group, propenyl group or an allyl group.

Furthermore, as described in the above, examples of $R^1$ include "an alkyl group having 1 to 6 carbon atoms, which is substituted with at least one $-SiR^{18}R^{19}R^{20}$ group (wherein $R^{18}$, $R^{19}$ and $R^{20}$ each independently represent an alkyl group having 1 to 6 carbon atoms, an alkenyl group having 2 to 6 carbon atoms, an alkoxy group having 1 to 6 carbon atoms or a phenyl group)" and "a haloalkyl group having 1 to 6 carbon atoms, which is substituted with at least one $-SiR^{18}R^{19}R^{20}$ group (wherein $R^{18}$, $R^{19}$ and $R^{20}$ each independently represent an alkyl group having 1 to 6 carbon atoms, an alkenyl group having 2 to 6 carbon atoms, an alkoxy group having 1 to 6 carbon atoms or a phenyl group)".

However, $R^1$ is more preferably "an alkyl group having 1 to 6 carbon atoms, which is substituted with one $-SiR^{18}R^{19}R^{20}$ group (wherein $R^{18}$, $R^{19}$ and $R^{20}$ each independently represent a methyl group, an ethyl group, a linear or branched propyl group, a linear or branched butyl group, a vinyl group, an allyl group, a methoxy group, an ethoxy group, a phenoxy group or a phenyl group)" or "a fluoroalkyl group having 1 to 6 carbon atoms, which is substituted with one $-SiR^{18}R^{19}R^{20}$ group (wherein $R^{18}$, $R^{19}$ and $R^{20}$ each independently represent a methyl group, an ethyl group, a linear or branched propyl group, a linear or branched butyl group, a vinyl group, an allyl group, a methoxy group, an ethoxy group, a phenoxy group or a phenyl group)".

$R^1$ is particularly preferably "a methyl group which is substituted with one —SiR$^{18}$R$^{19}$R$^{20}$ group (wherein R$^{18}$, R$^{19}$ and R$^{20}$ each independently represent a methyl group, an ethyl group, a linear or branched propyl group, a linear or branched butyl group, a vinyl group, an allyl group or a phenyl group)", "a fluoromethyl group which is substituted with one —SiR$^{18}$R$^{19}$R$^{20}$ group (wherein R$^{18}$, R$^{19}$ and R$^{20}$ each independently represent a methyl group, an ethyl group, a linear or branched propyl group, a linear or branched butyl group, a vinyl group, an allyl group or a phenyl group)" or "a difluoromethyl group which is substituted with one —SiR$^{18}$R$^{19}$R$^{20}$ group (wherein R$^{18}$, R$^{19}$ and R$^{20}$ each independently represent a methyl group, an ethyl group, a linear or branched propyl group, a linear or branched butyl group, a vinyl group, an allyl group or a phenyl group)".

Furthermore, as described in the above, an example of R$^1$ is "a 5- or 6-membered heterocyclic group (which may or may not be substituted); however, R$^1$ is more preferably "a 5- or 6-membered heterocyclic group (wherein the heterocyclic group is a furyl group, a thienyl group, a pyrrolyl group, an oxazolyl group, an isoxazolyl group, a thiazolyl group, an isothiazolyl group, an imidazolyl group, a pyrazolyl group, a triazolyl group, a tetrazolyl group, a pyridyl group, a pyrimidinyl group, a pyrazinyl group, a pyridazinyl group or a triazinyl group and may be substituted with a fluorine atom, an alkyl group having 1 to 6 carbon atoms or a fluoroalkyl group having 1 to 6 carbon atoms)", particularly preferably "a thienyl group (which may be substituted with a fluorine atom, an alkyl group having 1 to 6 carbon atoms or a fluoroalkyl group having 1 to 6 carbon atoms) or a pyridyl group (which may be substituted with a fluorine atom, an alkyl group having 1 to 6 carbon atoms or a fluoroalkyl group having 1 to 6 carbon atoms)".

Furthermore, as described in the above, an example of R$^1$ is "a group represented by any one of the Formulae (3-1) to (3-10)" and R$^a$ in the Formulae (3-1) to (3-10) is "a divalent hydrocarbon group having 1 to 12 carbon atoms which may be substituted with a halogen atom".

R$^a$ is preferably an alkylene group having 1 to 6 carbon atoms, a fluoroalkylene group having 1 to 6 carbon atoms, a phenylene group (which may be substituted with a fluorine atom, an alkyl group having 1 to 6 carbon atoms or a fluoroalkyl group having 1 to 6 carbon atoms) or an alkenylene group having 2 to 6 carbon atoms. R$^a$ is more preferably a methylene group, an ethylene group, a propylene group, a butylene group, a fluoromethylene group, a difluoromethylene group, a perfluoroethylene group or a phenylene group (which may be substituted with a fluorine atom, a methyl group, an ethyl group, a propyl group, a butyl group or a trifluoromethyl group).

Furthermore, as described in the above, an example of R$^1$ is "a group represented by any one of the Formulae (3-1) to (3-10)" and R$^b$ in the Formulae (3-1) to (3-10) is "a hydrocarbon group having 1 to 12 carbon atoms which may be substituted with a halogen atom or a —SiR$^{21}$R$^{22}$R$^{23}$ group (wherein R$^{21}$, R$^{22}$ and R$^{23}$ each independently represent an alkyl group having 1 to 6 carbon atoms, an alkenyl group having 2 to 6 carbon atoms, an alkoxy group having 1 to 6 carbon atoms or a phenyl group)".

R$^b$ is preferably an alkyl group having 1 to 6 carbon atoms, a fluoroalkyl group having 1 to 6 carbon atoms, a phenyl group (which may be substituted with a fluorine atom, an alkyl group having 1 to 6 carbon atoms or a fluoroalkyl group having 1 to 6 carbon atoms), an alkenyl group having 2 to 6 carbon atoms or a —SiR$^{21}$R$^{22}$R$^{23}$ group (wherein R$^{21}$, R$^{22}$ and R$^{23}$ are each independently an alkyl group having 1 to 6 carbon atoms, an alkenyl group having 2 to 6 carbon atoms, an alkoxy group having 1 to 6 carbon atoms or a phenyl group). R$^b$ is more preferably a methyl group, an ethyl group, a propyl group, a butyl group, a trifluoromethyl group, a perfluoroethyl group, a phenyl group (which may be substituted with a fluorine atom, a methyl group, an ethyl group, a propyl group, a butyl group or a trifluoromethyl group), a vinyl group, a propenyl group or a —SiR$^{21}$R$^{22}$R$^{23}$ group (wherein R$^{21}$, R$^{22}$ and R$^{23}$ are each independently a methyl group, an ethyl group, a linear or branched propyl group, a linear or branched butyl group, a vinyl group, a propenyl group, an allyl group, a methoxy group, an ethoxy group or a phenyl group).

As for m and n in the Formula (1), as described in the above, there are two types of combinations, <m=0, n=2> and <m=1, n=1>; however, the combination of <m=0, n=2> is more preferred.

Preferred combinations of m, n, R$^1$ and R$^3$ to R$^5$ in the Formula (1) will now be described from the viewpoints of enabling to attain an improvement in the battery output characteristics by reducing the battery resistance, and inhibiting deterioration of performance in a high-temperature environment.

Examples of preferred combinations in the Formula (1) include those in which m is 0; n is 2;

R$^1$ is an alkyl group having 1 to 6 carbon atoms, a fluoroalkyl group having 1 to 6 carbon atoms, an aryl group having 6 to 14 carbon atoms (which may be substituted with a fluorine atom, an alkyl group having 1 to 6 carbon atoms or a fluoroalkyl group having 1 to 6 carbon atoms), an alkenyl group having 2 to 6 carbon atoms, an alkyl group having 1 to 6 carbon atoms, which is substituted with one —SiR$^{18}$R$^{19}$R$^{20}$ group (wherein R$^{18}$, R$^{19}$ and R$^{20}$ each independently represent an alkyl group having 1 to 6 carbon atoms, an alkenyl group having 2 to 6 carbon atoms, an alkoxy group having 1 to 6 carbon atoms or a phenyl group), a fluoroalkyl group having 1 to 6 carbon atoms, which is substituted with one —SiR$^{18}$R$^{19}$R$^{20}$ group (wherein R$^{18}$, R$^{19}$ and R$^{20}$ each independently represent an alkyl group having 1 to 6 carbon atoms, an alkenyl group having 2 to 6 carbon atoms, an alkoxy group having 1 to 6 carbon atoms or a phenyl group), a 5- or 6-membered heterocyclic group (wherein the heterocyclic group is a furyl group, a thienyl group, a pyrrolyl group, an oxazolyl group, an isoxazolyl group, a triazolyl group, an isothiazolyl group, an imidazolyl group, a pyrazolyl group, a triazolyl group, a tetrazolyl group, a pyridyl group, a pyrimidinyl group, a pyrazinyl group, a pyridazinyl group or a triazinyl group and may be substituted with a fluorine atom, an alkyl group having 1 to 6 carbon atoms or a fluoroalkyl group having 1 to 6 carbon atoms), or a group represented by any one of the Formulae (3-1), (3-9) and (3-10), with the proviso that, in the Formulae (3-1), (3-9) and (3-10), R$^a$ is an alkylene group having 1 to 6 carbon atoms, a fluoroalkylene group having 1 to 6 carbon atoms, a phenylene group (which may be substituted with a fluorine atom, an alkyl group having 1 to 6 carbon atoms or a fluoroalkyl group having 1 to 6 carbon atoms) or an alkenylene group having 2 to 6 carbon atoms, and R$^h$ is an alkyl group having 1 to 6 carbon atoms, a fluoroalkyl group having 1 to 6 carbon atoms, a phenyl group (which may be substituted with a fluorine atom, an alkyl group having 1 to 6 carbon atoms or a fluoroalkyl group having 1 to 6 carbon atoms), an alkenyl group having 2 to 6 carbon atoms or a —SiR$^{21}$R$^{22}$R$^{23}$ group (wherein R$^{21}$, R$^{22}$ and R$^{23}$ are each independently an alkyl group having 1 to 6 carbon atoms, an alkenyl group having 2 to 6 carbon atoms, an alkoxy group having 1 to 6 carbon atoms or a phenyl group); and $R^3$ to $R^5$ have the same definitions as described in the above.

Among the above-described combinations, a particularly preferred combination is one in which m is 0; n is 2;

$R^1$ is an alkyl group having 1 to 6 carbon atoms, a fluoroalkyl group having 1 to 6 carbon atoms, an aryl group having 6 to 14 carbon atoms (which may be substituted with a fluorine atom, an alkyl group having 1 to 6 carbon atoms or a fluoroalkyl group having 1 to 6 carbon atoms), an alkenyl group having 2 to 6 carbon atoms, an alkyl group having 1 to 6 carbon atoms, which is substituted with one —$SiR^{18}R^{19}R^{20}$ group (wherein $R^{18}$, $R^{19}$ and $R^{20}$ are each independently an alkyl group having 1 to 6 carbon atoms), a fluoroalkyl group having 1 to 6 carbon atoms, which is substituted with one —$SiR^{18}R^{19}R^{20}$ group (wherein $R^{18}$, $R^{19}$ and $R^{20}$ are each independently an alkyl group having 1 to 6 carbon atoms), or a group represented by any one of the Formulae (3-1), (3-9) and (3-10), with the proviso that, in the Formulae (3-1), (3-9) and (3-10), $R^a$ is an alkylene group having 1 to 6 carbon atoms, and $R^h$ is an alkyl group having 1 to 6 carbon atoms or a —$SiR^{21}R^{22}R^{23}$ group (wherein $R^{21}$, $R^{22}$ and $R^{23}$ are each independently an alkyl group having 1 to 6 carbon atoms); and $R^3$, $R^4$ and $R^5$ are each independently an alkyl group having 1 to 6 carbon atoms, an alkenyl group having 2 to 6 carbon atoms or a phenyl group.

Specific examples of the compound represented by the Formula (1) will now be provided; however, the present invention is not restricted thereto.

The following examples are shown by the combination of m and n.

The following Formula (1a) represents a compound having a combination of <m=0, n=2> in the Formula (1) and Compound Nos. 1 to 143 (hereinafter, also referred to as "Example Compounds 1 to 143", respectively) are specific examples thereof.

The following Formula (1b) represents a compound having a combination of <m=1, n=1> in the Formula (1) and Compound Nos. 144 to 168 (hereinafter, also referred to as "Example Compounds 144 to 168", respectively) are specific examples thereof.

It is noted here that, in the Compound Nos. 1 to 168 (Example Compounds 1 to 168), "Me", "Et", "t-Bu", "Ph", "Vinyl" and "Allyl" represent a methyl group, an ethyl group, a tert-butyl group, a phenyl group, a vinyl group and an allyl group, respectively.

Furthermore, in the column of $R^1$, "(3-1)" to "(3-10)" represents the Formulae (3-1) to (3-10), respectively. The columns of $R^a$ and $R^b$ represent $R^a$ and $R^b$ in the Formulae (3-1) to (3-10), respectively.

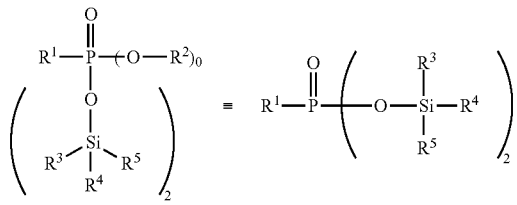

(1a)

| Compound No. | $R^1$ | $R^a$ | $R^b$ | $R^3$ | $R^4$ | $R^5$ |
|---|---|---|---|---|---|---|
| 1 | H | — | — | Me | Me | Me |
| 2 | Me | — | — | Me | Me | Me |
| 3 | Me | — | — | Me | Me | t-Bu |
| 4 | Me | — | — | Me | Me | Vinyl |
| 5 | Me | — | — | Me | Me | Allyl |
| 6 | Me | — | — | Me | Me | Ph |
| 7 | Me | — | — | Me | Ph | Ph |
| 8 | Me | — | — | Ph | Ph | Ph |
| 9 | Et | — | — | Me | Me | Me |
| 10 | Et | — | — | Ph | Ph | Ph |
| 11 | $CH_3CH_2CH_2$ | — | — | Me | Me | Me |
| 12 | t-Bu | — | — | Me | Me | Me |
| 13 | $CH_2F$ | — | — | Me | Me | Me |
| 14 | $CHF_2$ | — | — | Me | Me | Me |
| 15 | $CF_3$ | — | — | Me | Me | Me |
| 16 | $CBrF_2$ | — | — | Me | Me | Me |
| 17 | $CF_3CH_2$ | — | — | Me | Me | Me |
| 18 | $CF_3CF_2$ | — | — | Me | Me | Me |
| 19 | Ph | — | — | Me | Me | Me |
| 20 | Ph | — | — | Me | Me | Vinyl |
| 21 | Ph | — | — | Me | Me | Allyl |
| 22 | Ph | — | — | Me | Me | Ph |
| 23 | Ph | — | — | Ph | Ph | Ph |
| 24 | (4-F)Ph | — | — | Me | Me | Me |
| 25 | (4-Cl)Ph | — | — | Me | Me | Me |
| 26 | (4-Me)Ph | — | — | Me | Me | Me |
| 27 | (4-Et)Ph | — | — | Me | Me | Me |
| 28 | (4-t-Bu)Ph | — | — | Me | Me | Me |
| 29 | (4-$CF_3$)Ph | — | — | Me | Me | Me |

-continued
| | | | | | | |
|---|---|---|---|---|---|---|
| 30 | CH$_2$=CH | — | — | Me | Me | Me |
| 31 | CH$_3$—CH=CH | — | — | Me | Me | Me |
| 32 | CH$_2$=CH—CH$_2$ | — | — | Me | Me | Me |
| 33 | (Me$_3$Si)CH$_2$ | — | — | Me | Me | Me |
| 34 | (Me$_3$Si)CF$_2$ | — | — | Me | Me | Me |
| 35 | (Me$_3$Si)CH$_2$CH$_2$ | — | — | Me | Me | Me |
| 36 | (Me$_3$Si)CF$_2$CF$_2$ | — | — | Me | Me | Me |
| 37 | (Et$_3$Si)CH$_2$ | — | — | Me | Me | Me |
| 38 | (Et$_3$Si)CF$_2$ | — | — | Me | Me | Me |
| 39 | (Ph$_3$Si)CH$_2$CH$_2$ | — | — | Me | Me | Me |
| 40 | (Ph$_3$Si)CF$_2$CF$_2$ | — | — | Me | Me | Me |
| 41 | 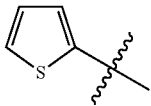 [SMILES: *c1cccs1] | — | — | Me | Me | Me |
| 42 | 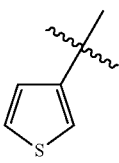 | — | — | Me | Me | Me |
| 43 | 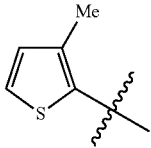 [SMILES: *c1sccc1C] | — | — | Me | Me | Me |
| 44 | 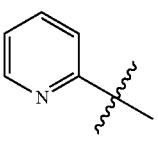 | — | — | Me | Me | Me |
| 45 | 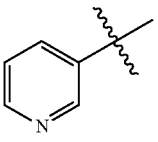 [SMILES: *c1cccnc1] | — | — | Me | Me | Me |
| 46 | 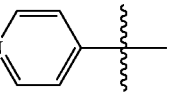 | — | — | Me | Me | Me |
| 47 | 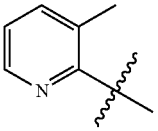 | — | — | Me | Me | Me |
| 48 | 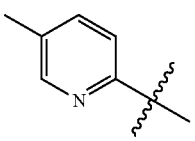 [SMILES: *c1ccc(C)cn1] | — | — | Me | Me | Me |
| 49 | 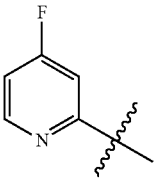 [SMILES: *c1cc(F)ccn1] | — | — | Me | Me | Me |

-continued

| | | | | | | |
|---|---|---|---|---|---|---|
| 50 | 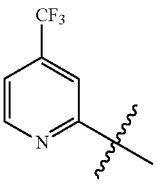 | — | — | Me | Me | Me |
| 51 | 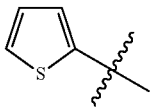 [SMILES: *c1cccs1] | — | — | Me | | Me |
| 52 | 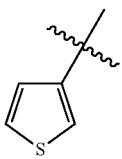 | — | — | Me | Me | Me |
| 53 | 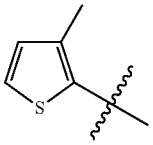 [SMILES: *c1sccc1C] | — | — | Me | Me | Me |
| 54 | (3-1) | CH$_2$ | Me | Me | Me | Me |
| 55 | (3-1) | CH$_2$CH$_2$ | Me | Me | Me | Me |
| 56 | (3-1) | CF$_2$ | Me | Me | Me | Me |
| 57 | (3-1) | CH$_2$ | SiMe$_3$ | Me | Me | Me |
| 58 | (3-1) | CH$_2$ | SiMe$_3$ | Me | Me | t-Bu |
| 59 | (3-1) | CH$_2$ | SiMe$_2$(t-Bu) | Me | Me | Me |
| 60 | (3-1) | CH$_2$ | SiMe$_3$ | Ph | Ph | Ph |
| 61 | (3-2) | CH$_2$ | Me | Me | Me | Me |
| 62 | (3-2) | CH$_2$ | Et | Me | Me | Me |
| 63 | (3-2) | CH$_2$ | Ph | Me | Me | Me |
| 64 | (3-2) | Phenylene | Me | Me | Me | Me |
| 65 | (3-2) | Phenylene | CF$_3$ | Me | Me | Me |
| 66 | (3-3) | CH$_2$ | Me | Me | Me | Me |
| 67 | (3-3) | CH$_2$ | Et | Me | Me | Me |
| 68 | (3-3) | Phenylene | Me | Me | Me | Me |
| 69 | (3-3) | Phenylene | SiMe$_3$ | Me | Me | Me |
| 70 | (3-4) | CH$_2$ | Me | Me | Me | Me |
| 71 | (3-4) | Phenylene | Me | Me | Me | Me |
| 72 | (3-5) | CH$_2$ | Me | Me | Me | Me |
| 73 | (3-5) | CH$_2$ | Ph | Me | Me | Me |
| 74 | (3-6) | CH$_2$ | Me | Me | Me | Me |
| 75 | (3-6) | CH$_2$ | Et | Me | Me | Me |
| 76 | (3-6) | CH$_2$ | Ph | Me | Me | Me |
| 77 | (3-6) | CH$_2$ | SiMe$_3$ | Me | Me | Me |
| 78 | (3-6) | CF$_2$ | Me | Me | Me | Me |
| 79 | (3-6) | CF$_2$ | Et | Me | Me | Me |
| 80 | (3-6) | CF$_2$ | Ph | Me | Me | Me |
| 81 | (3-6) | CF$_2$ | SiMe$_3$ | Me | Me | Me |
| 82 | (3-6) | CF$_2$ | SiPh$_3$ | Me | Me | Me |
| 83 | (3-7) | CH$_2$ | Me | Me | Me | Me |
| 84 | (3-7) | CH$_2$ | Et | Me | Me | Me |
| 85 | (3-7) | CH$_2$ | Ph | Me | Me | Me |
| 86 | (3-7) | CF$_2$ | Me | Me | Me | Me |
| 87 | (3-7) | CF$_2$ | Et | Me | Me | Me |
| 88 | (3-7) | Phenylene | Ph | Me | Me | Me |
| 89 | (3-8) | CH$_2$ | Me | Me | Me | Me |
| 90 | (3-8) | CH$_2$ | Et | Me | Me | Me |
| 91 | (3-8) | CH$_2$ | Me | Me | Me | Me |
| 92 | (3-8) | CH$_2$ | Et | Me | Me | Me |
| 93 | (3-8) | Phenylene | Me | Me | Me | Me |
| 94 | (3-8) | Phenylene | Ph | Me | Me | Me |
| 95 | (3-9) | CH$_2$ | Me | Me | Me | Me |
| 96 | (3-9) | CH$_2$ | Et | Me | Me | Me |
| 97 | (3-9) | CH$_2$ | CF$_3$ | Me | Me | Me |
| 98 | (3-9) | CH$_2$ | Ph | Me | Me | Me |
| 99 | (3-9) | CH$_2$ | SiMe$_3$ | Me | Me | Me |
| 100 | (3-9) | CH$_2$CH$_2$ | Me | Me | Me | Me |
| 101 | (3-9) | CH$_2$CH$_2$ | CF$_3$ | Me | Me | Me |

-continued

| | | | | | | | |
|---|---|---|---|---|---|---|---|
| 102 | (3-9) | CH₂CH₂ | (4-Me)Ph | Me | Me | Me | |
| 103 | (3-9) | Phenylene | Me | Me | Me | Me | |
| 104 | (3-9) | Phenylene | CF₃ | Me | Me | Me | |
| 105 | (3-9) | Phenylene | (4-Me)Ph | Me | Me | Me | |
| 106 | (3-9) | CF₂ | Me | Me | Me | Me | |
| 107 | (3-9) | CF₂ | Ph | Me | Me | Me | |
| 108 | (3-10) | CH₂ | Et | Me | Me | Me | |
| 109 | (3-10) | CH₂ | SiMe₃ | Me | Me | Me | |
| 110 | (3-10) | CF₂ | Et | Me | Me | Me | |
| 111 | (3-10) | CF₂ | SiMe₃ | Me | Me | Me | |
| 112 | (3-10) | CH₂CH₂ | Et | Me | Me | Me | |
| 113 | (3-10) | CH₂CH₂ | SiMe₃ | Me | Me | Me | |
| 114 | (3-1) | CH₂ | Me | Me | Me | t-Bu | |
| 115 | (3-1) | CF₂ | Me | Ph | Ph | Ph | |
| 116 | (3-2) | CH₂ | Me | Me | Me | t-Bu | |
| 117 | (3-2) | CH₂ | Me | Me | Me | Ph | |
| 118 | (3-2) | Phenylene | Me | Me | Me | t-Bu | |
| 119 | (3-3) | CH₂ | Me | Me | Me | t-Bu | |
| 120 | (3-3) | CH₂ | Me | Ph | Ph | Ph | |
| 121 | (3-4) | CH₂ | Me | Ph | Ph | Ph | |
| 122 | (3-4) | Phenylene | Me | Ph | Ph | Ph | |
| 123 | (3-5) | CH₂ | Me | Me | Me | t-Bu | |
| 124 | (3-6) | CH₂ | Me | Me | Me | t-Bu | |
| 125 | (3-6) | CH₂ | Me | Me | Me | Ph | |
| 126 | (3-6) | CH₂ | Me | Me | Ph | Ph | |
| 127 | (3-6) | CH₂ | Me | Ph | Ph | Ph | |
| 128 | (3-7) | CH₂ | Me | Me | Me | t-Bu | |
| 129 | (3-7) | CF₂ | Me | Me | Me | t-Bu | |
| 130 | (3-7) | CF₂ | Me | Me | Me | Ph | |
| 131 | (3-7) | CF₂ | Me | Ph | Ph | Ph | |
| 132 | (3-8) | CH₂ | Me | Me | Me | t-Bu | |
| 133 | (3-8) | CH₂ | Et | Me | Me | t-Bu | |
| 134 | (3-9) | CH₂ | Me | Me | Me | t-Bu | |
| 135 | (3-9) | CH₂ | Me | Me | Me | Ph | |
| 136 | (3-9) | CH₂ | CF₃ | Me | Me | t-Bu | |
| 137 | (3-9) | CH₂ | CF₃ | Me | Me | Ph | |
| 138 | (3-10) | CH₂ | Et | Me | Me | t-Bu | |
| 139 | (3-10) | CH₂ | SiPh₃ | Ph | Ph | Ph | |
| 140 | Me | — | — | Me | Me | OMe | |
| 141 | Me | — | — | Me | MeO | OMe | |
| 142 | Me | — | — | MeO | MeO | OMe | |
| 143 | Me | — | — | Me | Me | OSiMe₃ | |

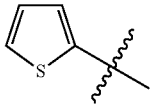 [SMILES: *c1cccs1]

(1b)

| Compound No. | $R^1$ | $R^a$ | $R^b$ | $R^2$ | $R^3$ | $R^4$ | $R^5$ |
|---|---|---|---|---|---|---|---|
| 144 | Me | — | — | Me | Me | Me | Me |
| 145 | Me | — | — | Et | Me | Me | Me |
| 146 | Me | — | — | Ph | Me | Me | Me |
| 147 | Me | — | — | CF₃ | Me | Me | Me |
| 148 | Me | — | — | Allyl | Me | Me | Me |
| 149 | Ph | — | — | Me | Me | Me | Me |
| 150 | Ph | — | — | CF₃ | Me | Me | Me |
| 151 | Ph | — | — | Ph | Me | Me | Me |
| 152 | Ph | — | — | Et | Me | Me | t-Bu |
| 153 | Ph | — | — | Et | Me | Me | Ph |
| 154 | Ph | — | — | Et | Ph | Ph | Ph |
| 155 | 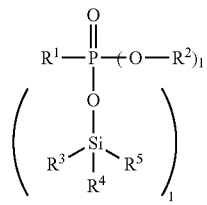 | — | — | Et | Me | Me | Me |

-continued

| | | | | | | | |
|---|---|---|---|---|---|---|---|
| 156 | 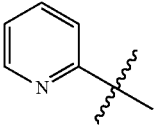 | — | — | Et | Me | Me | Me |
| 157 | 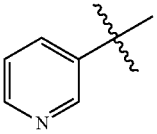 | — | — | Et | Me | Me | Me |
| 158 | (3-1) | CH$_2$ | Me | Et | Me | Me | Me |
| 159 | (3-2) | CH$_2$ | Me | Et | Me | Me | Me |
| 160 | (3-3) | CH$_2$ | Me | Et | Me | Me | Me |
| 161 | (3-4) | CH$_2$ | Me | Et | Me | Me | Me |
| 162 | (3-5) | CH$_2$ | Me | Et | Me | Me | Me |
| 163 | (3-6) | CH$_2$ | Me | Et | Me | Me | Me |
| 164 | (3-7) | CH$_2$ | Me | Et | Me | Me | Me |
| 165 | (3-8) | CH$_2$ | Me | Et | Me | Me | Me |
| 166 | (3-9) | CH$_2$ | Me | Et | Me | Me | Me |
| 167 | (3-10) | CH$_2$ | Me | Et | Me | Me | Me |
| 168 | (3-4) | CH$_2$ | Et | Et | Me | Me | Me |

Among the compounds having a combination of <m=0, n=2> in the above-described Formula (1), specific examples of the compound represented by the above-described Formula (2) (Compound Nos. 169 to 202; hereinafter, also referred to as "Example Compounds 169 to 202", respectively) will now be provided; however, the present invention is not restricted thereto.

It is noted here that, in the Example Compounds 169 to 202, "Me", "Et", "i-Pr", "t-Bu", "Ph", "Vinyl" and "Allyl" represent a methyl group, an ethyl group, an isopropyl group, a tert-butyl group, a phenyl group, a vinyl group and an allyl group, respectively. Furthermore, in the column of X, "(X-1)" to "(X-26)" represent the above-described Formulae (X-1) to (X-26), respectively.

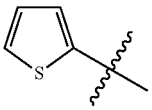 [SMILES: *c1cccs1]

(2)

| Compound No. | R$^1$ | R$^a$ | R$^b$ | X | R$^9$ | R$^{10}$ | R$^{11}$ | R$^{12}$ |
|---|---|---|---|---|---|---|---|---|
| 169 | Me | — | — | O | Me | Me | Me | Me |
| 170 | Me | — | — | CH$_2$ | Me | Me | Me | Me |
| 171 | Me | — | — | CH$_2$CH$_2$ | Me | Me | Me | Me |
| 172 | Me | — | — | CH$_2$CH$_2$CH$_2$ | Me | Me | Me | Me |
| 173 | Me | — | — | O | Vinyl | Me | Vinyl | Me |
| 174 | Me | — | — | O | Allyl | Me | Allyl | Me |
| 175 | Me | — | — | O | i-Pr | iPr | i-Pr | i-Pr |
| 176 | Me | — | — | O | Ph | Ph | Ph | Ph |
| 177 | Ph | — | — | O | Me | Me | Me | Me |
| 178 | Ph | — | — | CH$_2$ | Me | Me | Me | Me |
| 179 | Ph | — | — | CH$_2$CH$_2$ | Me | Me | Me | Me |
| 180 | CF$_3$ | — | — | O | Me | Me | Me | Me |
| 181 | Vinyl | — | — | O | Me | Me | Me | Me |
| 182 | 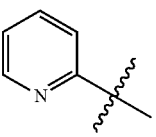 [SMILES: *c1ccccn1] | — | — | O | Me | Me | Me | Me |
| 183 |  | — | — | O | Me | Me | Me | Me |

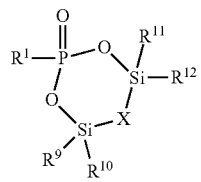

(2)

| Compound No. | $R^1$ | $R^a$ | $R^b$ | X | $R^9$ | $R^{10}$ | $R^{11}$ | $R^{12}$ |
|---|---|---|---|---|---|---|---|---|
| 184 | (3-1) | $CH_2$ | Me | O | Me | Me | Me | Me |
| 185 | (3-1) | $CH_2$ | $SiMe_3$ | O | Me | Me | Me | Me |
| 186 | (3-2) | $CH_2$ | Me | O | Me | Me | Me | Me |
| 187 | (3-3) | $CH_2$ | Me | O | Me | Me | Me | Me |
| 188 | (3-4) | $CH_2$ | Me | O | Me | Me | Me | Me |
| 189 | (3-5) | $CH_2$ | Me | O | Me | Me | Me | Me |
| 190 | (3-6) | $CH_2$ | Me | O | Me | Me | Me | Me |
| 191 | (3-7) | $CH_2$ | Me | O | Me | Me | Me | Me |
| 192 | (3-8) | $CH_2$ | Me | O | Me | Me | Me | Me |
| 193 | (3-9) | $CH_2$ | Me | O | Me | Me | Me | Me |
| 194 | (3-10) | $CH_2$ | Me | O | Me | Me | Me | Me |
| 195 | Me | — | — | (X-1) | Me | Me | Me | Me |
| 196 | Me | — | — | (X-10) | Me | Me | Me | Me |
| 197 | Me | — | — | (X-14) | Me | Me | Me | Me |
| 198 | Me | — | — | (X-19) | Me | Me | Me | Me |
| 199 | Me | — | — | (X-20) | Me | Me | Me | Me |
| 200 | (3-1) | $CH_2$ | Me | (X-1) | Me | Me | Me | Me |
| 201 | (3-7) | $CH_2$ | Me | (X-1) | Me | Me | Me | Me |
| 202 | (3-9) | $CH_2$ | Me | (X-1) | Me | Me | Me | Me |

The compounds having a combination of <m=0, n=2> in the above-described Formula (1) (including the compound represented by the Formula (2)) can be produced by a method described in the following known documents; however, the production method is not restricted thereto.

Tetrahedron Letters, 1977, p155-158

Bulletin of the Academy of Sciences of the USSR, Division of Chemical Science (English Translation), 1961, p952-956

Journal of the American Chemical Society, 1994, p1737-1741

Journal of Organic Chemistry, 1986, p4768-4779

Furthermore, those compounds having a combination of <m=1, n=1> in the Formula (1) can be, for example, synthesized by the following reaction route and then isolated and purified by an existing method such as distillation, recrystallization or column chromatography.

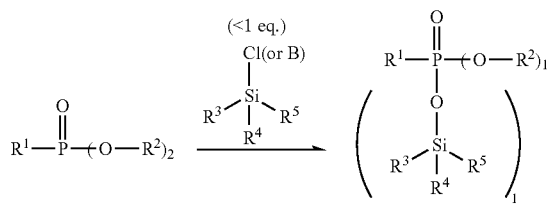

The compound represented by the Formula (1) (including the compound represented by the Formula (2)) is useful as an additive for lithium secondary batteries, and particularly as an additive for the non-aqueous electrolyte solution of lithium secondary batteries that will be described below. By adding this additive to a non-aqueous electrolyte solution, the battery resistance can be reduced and the battery storage properties in a high-temperature environment can be improved, so that an extended battery service life can be realized.

That is, the additive for lithium secondary batteries of the present invention is an additive for lithium secondary batteries containing the compound represented by the formula (I).

Furthermore, the additive for lithium secondary batteries of the present invention may contain, if necessary, other components in addition to the compound represented by the formula (I).

As these other components, from the viewpoint of attaining the above-described effects more effectively, for example, at least one selected from the group consisting of a tetrafluoroborate that will be described below, a compound represented by Formula (III) that will be described below, a compound represented by Formula (IV) and a compound represented Formula (V) that will be described below can be used.

The non-aqueous electrolyte solution of the present invention may contain only one kind of the silyl ester group-containing phosphonic acid derivative described above or may contain two or more kinds thereof.

The total content of the above-described silyl ester group-containing phosphonic acid derivative in the non-aqueous electrolyte solution of the present invention is preferably 0.001% by mass to 10% by mass, and more preferably in the range of 0.05% by mass to 5% by mass. In this range, an increase in battery resistance over time can be suppressed and an extended service life can be attained.

Next, other components of the non-aqueous electrolyte solution of the present invention will be described. Generally, a non-aqueous electrolyte solution contains an electrolyte and a non-aqueous solvent.

(Non-Aqueous Solvent)

The above-described non-aqueous solvent can be selected as appropriate from a variety of known non-aqueous solvents; however, it is preferably a cyclic aprotic solvent and/or a chain aprotic solvent.

In the case of promoting an increase of the flash point of the solvent for an enhancement of the safety of batteries, it is preferable to use a cyclic aprotic solvent as the non-aqueous solvent.

[Cyclic Aprotic Solvent]

As the above-described cyclic aprotic solvent, a cyclic carbonate, a cyclic carboxylic acid ester, a cyclic sulfone or a cyclic ether can be used.

The cyclic aprotic solvent may be used individually or plural thereof may be used in combination.

The mixing ratio of the cyclic aprotic solvent in the non-aqueous solvent is 10% by mass to 100% by mass, more preferably 20% by mass to 90% by mass, particularly preferably 30% by mass to 80% by mass. By controlling the mixing ratio in this range, the conductivity of an electrolyte solution, which relates to the battery charge-discharge characteristics, can be increased.

Specific examples of the cyclic carbonate include ethylene carbonate, propylene carbonate, 1,2-butylene carbonate, 2,3-butylene carbonate, 1,2-pentylene carbonate and 2,3-pentylene carbonate. Thereamong, ethylene carbonate and propylene carbonate that have a high dielectric constant are suitably used. In the case of a battery in which graphite is used as a negative electrode active material, ethylene carbonate is more preferred. Furthermore, these cyclic carbonates may be used as mixtures of two or more kinds.

Specific examples of cyclic carboxylic acid esters include γ-butyrolactone, δ-valerolactone, and alkyl-substituted compounds such as methyl-γ-butyrolactone, ethyl-γ-butyrolactone, and ethyl-δ-valerolactone.

The cyclic carboxylic acid esters have low vapor pressures, low viscosities, and high dielectric constants. These compounds can lower the viscosity of an electrolyte solution without lowering the flash point of the electrolyte solution and the degree of dissociation of the electrolyte. For this reason, the cyclic carboxylic acid esters have a feature that the conductivity of the electrolyte solution, which is an index related to the discharge characteristics of a battery, can be increased without increasing inflammability of the electrolyte solution. Therefore, in the case of promoting an increase in the flash point of the solvent, it is preferable to use a cyclic carboxylic acid ester as the cyclic aprotic solvent. γ-butyrolactone is most preferred.

Furthermore, the cyclic carboxylic acid ester is preferably used as a mixture with another cyclic aprotic solvent. For example, a mixture of a cyclic carboxylic acid ester and a cyclic carbonate and/or a chain carbonate may be used.

Specific examples of such combination of a cyclic carboxylic acid ester, a cyclic carbonate and/or a chain carbonate include combinations of: γ-butyrolactone and ethylene carbonate; γ-butyrolactone, ethylene carbonate and dimethyl carbonate; γ-butyrolactone, ethylene carbonate and methylethyl carbonate; γ-butyrolactone, ethylene carbonate and diethyl carbonate; γ-butyrolactone and propylene carbonate; γ-butyrolactone, propylene carbonate and dimethyl carbonate; γ-butyrolactone, propylene carbonate and methylethyl carbonate; γ-butyrolactone, propylene carbonate and diethyl carbonate; γ-butyrolactone, ethylene carbonate and propylene carbonate; γ-butyrolactone, ethylene carbonate, propylene carbonate and dimethyl carbonate; γ-butyrolactone, ethylene carbonate, propylene carbonate and methylethyl carbonate; γ-butyrolactone, ethylene carbonate, propylene carbonate and diethyl carbonate; γ-butyrolactone, ethylene carbonate, dimethyl carbonate and methylethyl carbonate; γ-butyrolactone, ethylene carbonate, dimethyl carbonate and diethyl carbonate; γ-butyrolactone, ethylene carbonate, methylethyl carbonate and diethyl carbonate; γ-butyrolactone, ethylene carbonate, dimethyl carbonate, methylethyl carbonate and diethyl carbonate; γ-butyrolactone, ethylene carbonate, propylene carbonate, dimethyl carbonate and methylethyl carbonate; γ-butyrolactone, ethylene carbonate, propylene carbonate, dimethyl carbonate and diethyl carbonate; γ-butyrolactone, ethylene carbonate, propylene carbonate, methylethyl carbonate and diethyl carbonate; γ-butyrolactone, ethylene carbonate, propylene carbonate, dimethyl carbonate, methylethyl carbonate and diethyl carbonate; γ-butyrolactone and sulfolane; γ-butyrolactone, ethylene carbonate and sulfolane; γ-butyrolactone, propylene carbonate and sulfolane; γ-butyrolactone, ethylene carbonate, propylene carbonate and sulfolane; and γ-butyrolactone, sulfolane and dimethyl carbonate.

Examples of the cyclic sulfone include sulfolanes, 2-methylsulfolane, 3-methylsulfolane, dimethyl sulfone, diethyl sulfone, dipropyl sulfone, methylethyl sulfone and methylpropyl sulfone.

Examples of the cyclic ether include dioxolanes.

[Chain Aprotic Solvent]

As the above-described chain aprotic solvent, for example, a chain carbonate, a chain carboxylic acid ester, a chain ether or a chain phosphoric acid ester can be used.

The mixing ratio of the chain aprotic solvent in the non-aqueous solvent is 10% by mass to 100% by mass, more preferably 20% by mass to 90% by mass, particularly preferably 30% by mass to 80% by mass.

Specific examples of the chain carbonate include dimethyl carbonate, methylethyl carbonate, diethyl carbonate, methylpropyl carbonate, methylisopropyl carbonate, ethylpropyl carbonate, dipropyl carbonate, methylbutyl carbonate, ethylbutyl carbonate, dibutyl carbonate, methylpentyl carbonate, ethylpentyl carbonate, dipentyl carbonate, methylheptyl carbonate, ethylheptyl carbonate, diheptyl carbonate, methylhexyl carbonate, ethylhexyl carbonate, dihexyl carbonate, methyloctyl carbonate, ethyloctyl carbonate, dioctyl carbonate and methyltrifluoroethyl carbonate. These chain carbonates may be used as mixtures of two or more kinds.

Specific examples of the chain carboxylic acid ester include methyl pivalate.

Specific examples of the chain ether include dimethoxyethanes.

Specific examples of the chain phosphoric acid ester include trimethyl phosphate.

[Combination of Solvents]

The non-aqueous solvent used in the non-aqueous electrolyte solution of the invention may be used singly or as a mixture of plural kinds. Furthermore, one kind or plural kinds of only cyclic aprotic solvents may be used, one kind or plural kinds of only chain aprotic solvents may be used, or a mixture of a cyclic aprotic solvent and a chain aprotic solvent may also be used. When it is intended to enhance the load characteristics and low temperature characteristics of a battery in particular, it is preferable to use a combination of a cyclic aprotic solvent and a chain aprotic solvent as the non-aqueous solvent.

Furthermore, in view of the electrochemical stability of the electrolyte solution, it is most preferable to apply a cyclic carbonate to the cyclic aprotic solvent, and to apply a chain carbonate to the linear aprotic solvent. Also, a combination of a cyclic carboxylic acid ester with a cyclic carbonate and/or a chain carbonate can also increase the conductivity of the electrolyte solution, which is related to the charge-discharge characteristics of the battery.

Specific examples of combination of a cyclic carbonate and a chain carbonate include combinations of: ethylene carbonate and dimethyl carbonate; ethylene carbonate and methylethyl carbonate; ethylene carbonate and diethyl carbonate; propylene carbonate and dimethyl carbonate; propylene carbonate and methylethyl carbonate; propylene carbonate and diethyl carbonate; ethylene carbonate, propylene carbonate and methylethyl carbonate; ethylene carbonate, propylene carbonate and diethyl carbonate; ethylene carbonate, dimethyl carbonate and methylethyl carbonate; ethylene carbonate, dimethyl carbonate and diethyl carbonate; ethylene carbonate, methylethyl carbonate and diethyl carbonate; ethylene carbonate, dimethyl carbonate, methylethyl carbonate and diethyl carbonate; ethylene carbonate, propylene carbonate, dimethyl carbonate and methylethyl carbonate; ethylene carbonate, propylene carbonate, dimethyl carbonate and diethyl carbonate; ethylene carbonate, propylene carbonate, methylethyl carbonate and diethyl carbonate; and ethylene carbonate, propylene carbonate, dimethyl carbonate, methylethyl carbonate and diethyl carbonate.

The mixing ratio of the cyclic carbonate and the chain carbonate is such that, when expressed as a mass ratio, the ratio of cyclic carbonate:chain carbonate is 5:95 to 80:20, more preferably 10:90 to 70:30, and particularly preferably 15:85 to 55:45. When such a ratio is used, an increase in the viscosity of the electrolyte solution is suppressed, and the degree of dissociation of the electrolyte can be increased. Therefore, the conductivity of the electrolyte solution related to the charge-discharge characteristics of the battery can be increased. Furthermore, the solubility of the electrolyte can be further increased. Accordingly, an electrolyte solution having excellent electrical conductivity at normal temperature or low temperatures can be obtained, and therefore, the load characteristics of a battery from normal temperature to low temperatures can be improved.

[Other Solvent]

In addition to the above-described solvents, the non-aqueous electrolyte solution of the present invention may also contain other solvent as non-aqueous solvent. Specific examples of the other solvent include amides such as dimethyl formamide; chain carbamates such as methyl-N,N-dimethyl carbamate; cyclic amides such as N-methyl pyrrolidone; cyclic ureas such as N,N-dimethylimidazolidinone; boron compounds such as trimethyl borate, triethyl borate, tributyl borate, trioctyl borate and trimethylsilyl borate; and polyethylene glycol derivatives represented by the following Formulae.

$$HO(CH_2CH_2O)_aH$$

$$HO[CH_2CH(CH_3)O]_bH$$

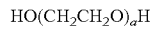

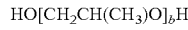

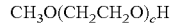

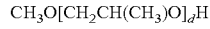

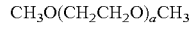

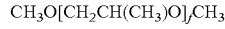

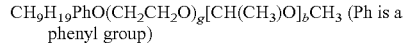

In the Formulae, a to f are each an integer from 5 to 250; g to j are each an integer from 2 to 249; $5 \leq g+h \leq 250$; and $5 \leq i+j \leq 250$.

(Electrolyte)

The non-aqueous electrolyte solution of the present invention may contain a variety of known electrolytes and any electrolyte may be used as long as it is normally used as an electrolyte for a non-aqueous electrolyte solution.

Specific examples of such electrolyte include tetraalkylammonium salts such as $(C_2H_5)_4NPF_6$, $(C_2H_5)_4NBF_4$, $(C_2H_5)_4NClO_4$, $(C_2H_5)_4NAsF_6$, $(C_2H_5)_4N_2SiF_6$, $(C_2H_5)_4NOSO_2C_kF_{(2k+1)}$ (k=an integer of 1 to 8) and $(C_2H_5)_4NPF_n[C_kF_{(2k+1)}]_{(6-n)}$ (n=1 to 5 and k=an integer of 1 to 8); lithium salts such as $LiPF_6$, $LiClO_4$, $LiAsF_6$, $Li_2SiF_6$, $LiOSO_2C_kF_{(2k+1)}$ (k=an integer of 1 to 8), $LiPF_n[C_kF_{(2k+1)}]_{(6-n)}$ (n=1 to 5 and k=an integer of 1 to 8), $LiC(SO_2R^{24})(SO_2R^{25})(SO_2R^{26})$, $LiN(SO_2OR^{27})(SO_2OR^{28})$ and $LiN(SO_2R^{29})(SO_2R^{30})$ (wherein $R^{24}$ to $R^{30}$ may be the same or different and are each a perfluoroalkyl group having 1 to 8 carbon atoms); and tetrafluoroborates such as $LiBF_4$, $NaBF_4$, $KBF_4$, $(C_4H_9)_4NBF_4$, $CH_3(C_2H_5)_3NBF_4$ and imidazolium tetrafluoroborate.

Examples of tetrafluoroborates include, as described in the above, $LiBF_4$, $NaBF_4$, $KBF_4$, $(C_4H_9)_4NBF_4$, $CH_3(C_2H_5)_3NBF_4$ and imidazolium tetrafluoroborate; however, considering the cost and the ease of handling, $LiBF_4$ is preferred.

As the electrolyte in the present invention, the above-described electrolytes may be used singly, or two or more kinds thereof may be used in combination.

In cases where the electrolyte is used singly, it is preferably $LiBF_6$ or $LiBF_4$.

In cases where two or more kinds of electrolytes are used in combination, the combination is preferably that of a lithium salt and a tetrafluoroborate, more preferably that of $LiPF_6$ and a tetrafluoroborate, particularly preferably that of $LiPF_6$ and $LiBF_4$.

The total electrolyte concentration in the non-aqueous electrolyte solution of the present invention is usually 0.1 mol/L to 3 mol/L, preferably 0.5 mol/L to 2 mol/L.

Furthermore, it is preferred that the electrolyte of the present invention contain at least one kind of tetrafluoroborate. This is because a reaction product generated by a reaction between the above-described silyl ester group-containing phosphonic acid derivative and the tetrafluoroborate ion modifies a coating film formed by an organic substance on the electrode surface into a coating film having an affinity for ions and, as a result, an increase in battery resistance can be further suppressed. Moreover, such a modified coating film of the electrode surface has further improved thermal stability, so that capacity reduction after storage at high temperature can be further suppressed.

In cases where the electrolyte contains at least one kind of tetrafluoroborate, the total electrolyte concentration, which is the concentration of the contained tetrafluoroborate and other electrolytes combined, may be any value as long as it is in the above-described range; however, it is desired that the concentration of the tetrafluoroborate be in the range of 0.0001 mol/L to 2 mol/L.

As long as the concentration of the tetrafluoroborate is not lower than 0.0001 mol/L, a higher concentration of the reaction product generated by a reaction between the above-described silyl ester group-containing phosphonic acid derivative and the tetrafluoroborate ion is attained, so that the above-described effects can be attained more effectively.

(Compound Represented by Formula (III))

From the viewpoint of forming a coating film on the negative electrode surface, it is preferred that the non-aqueous electrolyte solution of the present invention contain a compound represented by Formula (III).

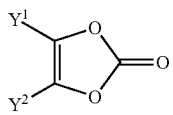

(III)

In the Formula (III), $Y^1$ and $Y^2$ independently represent a hydrogen atom, a methyl group, an ethyl group or a propyl group.

Examples of the compound represented by the Formula (III) include vinylene carbonate, methylvinylene carbonate, ethylvinylene carbonate, propylvinylene carbonate, dimethylvinylene carbonate, diethylvinylene carbonate and dipropylvinylene carbonate. Thereamong, vinylene carbonate is most preferred.

In cases where the non-aqueous electrolyte solution of the present invention contains a compound represented by the Formula (III), the content thereof in the non-aqueous electrolyte solution of the present invention can be selected as appropriate in accordance with the purpose thereof; however, it is preferably 0.001% by mass to 10% by mass, more preferably 0.05% by mass to 5% by mass.

(Compound Represented by Formula (IV))

From the viewpoint of forming a coating film on the negative electrode surface, it is preferred that the non-aqueous electrolyte solution of the present invention contain a compound represented by Formula (IV).

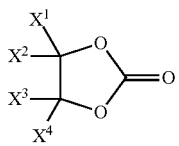

(IV)

In the Formula (IV), $X^1$, $X^2$, $X^3$ and $X^4$ each independently represent a hydrogen atom, a fluorine atom, a chlorine atom or an alkyl group having 1 to 3 carbon atoms which may be substituted with a fluorine atom. It is noted here, however, that all of $X^1$ to $X^4$ never are hydrogen atoms at the same time.

Examples of the alkyl group having 1 to 3 carbon atoms represented by $X^1$ to $X^4$ in the Formula (IV), which may be substituted with a fluorine atom, include fluoromethyl, difluoromethyl, trifluoromethyl, pentafluoroethyl and heptafluoropropyl.

As the compound represented by the Formula (IV), a known one can be used, and examples thereof include fluoroethylene carbonates in which 1 to 4 hydrogens in ethylene carbonate are substituted with fluorine, such as 4-fluoroethylene carbonate, 4,4-difluoroethylene carbonate, 4,5-difluoroethylene carbonate, 4,4,5-trifluoroethylene carbonate and 4,4,5,5-tetrafluoroethylene carbonate. Thereamong, most preferred are 4,5-difluoroethylene carbonate and 4-fluoroethylene carbonate.

In cases where the non-aqueous electrolyte solution of the present invention contains a compound represented by the Formula (IV), the content thereof in the non-aqueous electrolyte solution of the present invention can be selected as appropriate in accordance with the purpose thereof; however, it is preferably 0.001% by mass to 10% by mass, more preferably 0.05% by mass to 5% by mass.

(Compound Represented by Formula V)

From the viewpoint of forming a coating film on the surfaces of the positive and negative electrodes, it is preferred that the non-aqueous electrolyte solution of the present invention contain a compound represented by Formula (V).

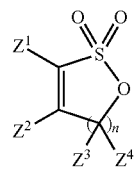

(V)

In the Formula (V), $Z^1$, $Z^2$, $Z^3$ and $Z^4$ are each independently an alkyl group having 1 to 12 carbon atoms which may contain a fluorine atom, a hydrogen atom or a fluorine atom, and n represents an integer of 0 to 3. When n is 2 or 3, the plural $Z^3$ and $Z^4$ may be the same or different.

Examples of the alkyl group having 1 to 12 carbon atoms represented by $Z^1$ to $Z^4$, which may contain a fluorine atom, include methyl group, ethyl group, n-propyl group, isopropyl group, n-butyl group, isobutyl group, sec-butyl group, tert-butyl group, pentyl group, 2-methylbutyl group, 1-methylpentyl group, neopentyl group, 1-ethylpropyl group, hexyl group, 3,3-dimethylbutyl group, heptyl group, octyl group, nonyl group, undecanyl group, dodecanyl group, fluoromethyl group, difluoromethyl group, trifluoromethyl group, 2,2,2-trifluoroethyl group, perfluoroethyl group, perfluoropropyl group, perfluorobutyl group, perfluoropentyl group, perfluorohexyl group, perfluoroheptyl group, perfluorooctyl group, perfluorononyl group, perfluorodecyl group, perfluoroundecanyl group, perfluorododecanyl group, perfluoroisopropyl group and perfluoroisobutyl group.

The number of carbon atoms in $Z^1$ to $Z^4$ is preferably 1 to 12; however, from the viewpoint of the solubility to the electrolyte solution, it is more preferably not more than 4, still more preferably not more than 2. It is most preferred that $Z^1$ to $Z^4$ be all hydrogen atoms.

The n is preferably 1 or 2, more preferably 1.

As the compound represented by the Formula (V), a known one can be used, and examples thereof include 1,3-prop-1-ene sultone, 3-methyl-1,3-prop-1-ene sultone, 4-methyl-1,3-prop-1-ene sultone, 5-methyl-1,3-prop-1-ene sultone and 1,4-butene-1-ene sultone. Thereamong, most preferred is 1,3-prop-1-ene sultone in which $Z^1$ to $Z^4$ are all hydrogen atoms and n is 1.

In cases where the non-aqueous electrolyte solution of the present invention contains a compound represented by the Formula (V), the content thereof in the non-aqueous electrolyte solution of the present invention can be selected as appropriate in accordance with the purpose thereof; however, it is preferably 0.001% by mass to 10% by mass, more preferably 0.05% by mass to 5% by mass.

The non-aqueous electrolyte solution of the present invention is not only suitable as a non-aqueous electrolyte solution for lithium secondary batteries, but can also be used as a non-aqueous electrolyte solution for primary batteries, a non-aqueous electrolyte solution for electrochemical capacitors, and an electrolyte solution for electric double-layer capacitors and aluminum electrolytic condensers.

<Lithium Secondary Battery>

The lithium secondary battery of the present invention is constituted to essentially include a negative electrode, a positive electrode, and the non-aqueous electrolyte solution of the invention, and usually, a separator is provided between the negative electrode and the positive electrode.

(Negative Electrode)

As a negative electrode active material constituting the negative electrode, at least one of lithium metal, lithium-containing alloys, metals or alloys that are capable of forming an alloy with lithium, oxides capable of doping/dedoping lithium ions, transition metal nitrides capable of doping/dedoping lithium ions and carbon materials capable of doping/dedoping lithium ions may be used.

Examples of the metals or alloys that are capable of forming an alloy with lithium ion include silicon, silicon alloys, tin and tin alloys. Examples of the oxides capable of doping/dedoping lithium ions include titanium-based oxides.

Thereamong, a carbon material capable of doping/dedoping lithium ions is preferred. Such carbon material may be a carbon black, an activated carbon, an artificial graphite, a natural graphite or an amorphous carbon and may also take any of a fibrous form, a spherical form, a potato-shape and a flake form.

Specific examples of the above-described amorphous carbon material include hard carbon, cokes, mesocarbon microbeads (MCMB) calcinated at 1,500° C. or lower and mesophase pitch carbon fiber (MCF).

Examples of graphite material include natural graphites and artificial graphites and, as an artificial graphite, a graphitized MCMB, a graphitized MCF or the like is used. Furthermore, as a graphite material, a boron-containing graphite material or the like may be used and a graphite material coated with a metal such as gold, platinum, silver, copper or tin, an amorphous carbon-coated graphite material or a mixture of amorphous carbon and graphite may also be used.

These carbon materials may be used singly, or two or more kinds may be used as a mixture. As the carbon material, particularly, one having an interplanar spacing d(002) between the (002) planes of not larger than 0.340 nm as measured by an X-ray analysis is preferred, and a graphite having a true density of not less than 1.70 g/cm$^3$ or a highly crystalline carbon material having properties similar to those of the graphite is preferred. By using such a carbon material, the energy density of a battery can be increased.

(Positive Electrode)

Examples of a positive electrode active material constituting the above-described positive electrode include transition metal oxides and transition metal sulfides such as $MoS_2$, $TiS_2$, $MnO_2$ and $V_2O_5$; complex oxides composed of lithium and transition metals such as $LiCoO_2$, $LiMnO_2$, $LiMn_2O_4$, $LiNiO_2$, $LiNi_xCo_{(1-x)}O_2$ [0<X<1] and $LiFePO_4$; and electroconductive polymer materials such as polyaniline, polythiophene, polypyrrole, polyacetylene, polyacene and dimercaptothiadiazole/polyaniline complex.

Thereamong, complex oxides composed of lithium and transition metals are particularly preferred.

In cases where the negative electrode is lithium metal or a lithium alloy, a carbon material may be used as the positive electrode. Furthermore, as the positive electrode, a mixture of a complex oxide composed of lithium and transition metals and a carbon material may also be used.

The positive electrode active material may be used singly, or two or more kinds may be used as a mixture. Since positive electrode active materials usually have insufficient conductivity, a positive electrode is constructed by using a positive electrode active material together with a conductive auxiliary agent. Examples of the conductive auxiliary agent include carbon materials such as carbon black, amorphous whisker, and graphite.

(Separator)

As the above-described separator, a film which electrically insulates the positive and negative electrodes from each other and allows lithium ions to pass therethrough can be used, and examples of such separator include a porous film and a polymer electrolyte.

As the above-described porous film, a microporous polymer film is suitably used, and examples of the material thereof include polyolefin, polyimide, polyvinylidene fluoride and polyester.

Particularly, a porous polyolefin is preferred, and specific examples thereof include a porous polyethylene film, a porous polypropylene film and a multilayer film containing a porous polyethylene film and a polypropylene film. On the porous polyolefin film, other resin having excellent thermostability may also be coated.

Examples of the above-described polymer electrolyte include a polymer in which a lithium salt is dissolved and a polymer swollen with an electrolyte solution.

The non-aqueous electrolyte solution of the present invention may also be used for the purpose of swelling a polymer to obtain a polymer electrolyte.

(Configuration of Battery)

The lithium secondary battery of the present invention includes the negative electrode active material, positive electrode active material, and separator described above.

The lithium secondary battery of the present invention may adopt various known shapes, and can be formed into a cylindrical shape, a coin shape, a box shape, a film shape, or any other shape. However, the fundamental structure of the battery is the same irrespective of the shape, and modification in the design can be applied in accordance with the purpose.

An example of the lithium secondary battery of the present invention may be a coin type battery illustrated in FIG. 1.

In the coin type battery shown in FIG. 1, a disc-shaped negative electrode 2, a separator 5 in which a non-aqueous electrolyte solution formed by dissolving a non-aqueous electrolyte in a non-aqueous solvent has been injected, a disc-shaped positive electrode 1, and optionally spacer plates 7 and 8 formed of stainless steel, aluminum or the like are accommodated, in the state of being laminated in this order, between a positive electrode can 3 (hereinafter, also referred to as "battery can") and a sealing plate 4 (hereinafter, also referred to as "battery can lid"). The positive electrode can 3 and the sealing plate 4 are sealed by caulking with a gasket 6.

The applications of the non-aqueous electrolyte solution of the exemplary embodiment of the present invention and a lithium secondary battery using the non-aqueous electrolyte solution are not particularly limited, and the non-aqueous electrolyte solution and the lithium secondary battery can be used in various known applications. For example, they can be widely used in small-sized portable equipment as well as large-sized equipment, such as laptop computers, mobile computers, mobile telephones, headphone stereo cassette players, video movie recorders, liquid crystal TV sets, handy cleaners, electronic organizers, calculators, radios, backup power supply applications, motors, automobiles, electric cars, motorcycles, electric motorcycles, bicycles, electric bicycles, lighting equipment, game machines, time pieces, electric tools, and cameras.

EXAMPLES

The present invention will now be described more concretely by way of examples thereof; however, the present invention is not restricted to these examples. It is noted here that, in the following examples, "%" means % by mass.

Synthesis of compounds represented by the Formula (1)

Synthesis of Example Compound 95

(Hydroxymethyl)phosphonic acid diethyl ester (20 mmol, 3.36 g) and triethyl amine (24 mmol, 2.42 g) were dissolved in methylene chloride and the resulting solution was cooled to 5° C. Then, methanesulfonyl chloride (24 mmol, 2.75 g) was added thereto dropwise. After stirring the resultant at 5° C. for 0.5 hour and then at room temperature for 1 hour, insoluble matters were removed by filtration. The thus obtained filtrate was washed with 1N hydrochloric acid, aqueous sodium bicarbonate solution and saturated saline, and then dried with magnesium sulfate. This magnesium sulfate was removed by filtration and an oily matter obtained by concentrating the filtrate was purified by silica gel column chromatography (ethyl acetate/n-hexane) to obtain colorless and transparent (methanesulfonyloxymethyl)phosphonic acid diethyl ester (yield: 3.77 g, 77%). The result of $^1$H-NMR measurement of this compound is shown below.

$^1$H-NMR (270 MHz, CDCl$_3$) δ (ppm): 4.44-4.41 (2H, d, J=8.9 Hz), 4.25-4.17 (4H, dt, J=1.1, 7.0 Hz), 3.12 (3H, s), 1.41-1.35 (6H, t, J=7.0 Hz)

The thus obtained (methanesulfonyloxymethyl)phosphonic acid diethyl ester (4.1 mmol, 1.0 g) was dissolved in 10 ml of dry methylene chloride and trimethylsilyl bromide (12.2 mmol, 1.86 g) was added thereto dropwise at room temperature. The resultant was stirred at room temperature for 5 hours and concentrated under reduced pressure. The resulting oily matter was vacuum-distilled (112 to 118° C./0.1 kPa) to obtain Example Compound 95 (yield: 0.87 g, 64%). The result of $^1$H-NMR measurement of the Example Compound 95 is shown below.

$^1$H-NMR (270 MHz, CDCl$_3$) δ (ppm): 4.28-4.24 (2H, d, J=9.5 Hz), 3.05 (3H, s), 0.27 (18H, s)

Synthesis of Example Compound 2

Methylphosphonic acid dimethyl ester (16.1 mmol, 2.0 g) was dissolved in 20 ml of dry methylene chloride and trimethylsilyl bromide (3 eq., 48.4 mmol, 7.4 g) was added thereto dropwise at room temperature. The resultant was stirred at room temperature for 5 hours and concentrated under reduced pressure. The resulting oily matter was vacuum-distilled (51 to 52° C./0.3 kPa) to obtain Example Compound 2 (yield: 2.46 g, 64%). The result of $^1$H-NMR measurement of the Example Compound 2 is shown below.

$^1$H-NMR (270 MHz, CDCl$_3$) δ (ppm): 1.41-1.35 (3H, d, J=17.8 Hz), 0.23 (18H, s)

Synthesis of Example Compound 3

In a flask equipped with Dean-Stark apparatus, methylphosphonic acid (15.6 mmol, 1.5 g) and tert-butyldimethyl silanol (2.1 eq., 32.8 mmol) were dissolved in 50 ml of dry n-hexane and the resultant was allowed to react under heating to reflux while isolating and eliminating distillated water. The thus obtained reaction solution was concentrated under reduced pressure (120° C./5.3 kPa) and the resulting oily matter was vacuum-distilled (97 to 100° C./0.2 kPa) to obtain Example Compound 3 (yield: 3.80 g, 75%). The result of $^1$H-NMR measurement of the Example Compound 3 is shown below.

$^1$H-NMR (270 MHz, CDCl$_3$) δ (ppm): 1.41-1.34 (311, d, J=17.8 Hz), 0.87 (18H, s), 020-0.19 (1211, d, J=2.4 Hz)

Synthesis of Example Compound 5

Methylphosphonic acid dimethyl ester (3.0 mmol, 0.37 g) was dissolved in 10 ml of dry methylene chloride and allyldimethylsilyl bromide (3 eq., 9.0 mmol, 1.62 g) was added thereto dropwise at room temperature. The resultant was stirred at room temperature for 5 hours and concentrated under reduced pressure. The resulting oily matter was vacuum-distilled (87 to 92° C./0.2 kPa) to obtain Example Compound 5 (yield: 0.47 g, 54%). The result of $^1$H-NMR measurement of the Example Compound 5 is shown below.

$^1$H-NMR (270 MHz, CDCl$_3$) δ (ppm): 5.87-5.71 (2H, m), 5.00-4.83 (4H, in), 1.77-1.75 (4H, d, J=7.8 Hz), 1.48-1.41 (3H, d, J=18.4 Hz), 0.30 (12H, s)

Synthesis of Example Compound 8

Methylphosphonic acid (10.0 mmol, 0.96 g) and ethoxytriphenyl silane (2.0 eq., 20.0 mmol, 6.09 g) were dissolved in 10 ml of dry o-xylene and the resultant was allowed to react under heating to reflux while distilling out distilled ethanol. The thus obtained reaction solution was cooled to room temperature and after adding thereto 40 ml of diethyl ether, the resultant was filtered to obtain a solid. The thus obtained solid was recrystallized from hot toluene to obtain Example Compound 8 (yield: 2.16 g, 35%). The result of $^1$H-NMR measurement of the Example Compound 8 is shown below.

$^1$H-NMR (270 MHz, CDCl$_3$) δ (ppm): 7.58-7.54 (12H, m), 7.46-7.39 (6H, m), 7.36-7.25 (12H, in), 1.28-1.21 (3H, d, J=18.1 Hz)

Synthesis of Example Compound 19

Example Compound 19 was synthesized in the same manner as the Example Compound 2, except that methylphosphonic acid dimethyl ester was changed to phenylphosphonic acid dimethyl ester and the conditions of the vacuum-distillation were changed to 85 to 91° C./0.2 kPa (yield: 41%). The result of $^1$H-NMR measurement of the Example Compound 19 is shown below.

$^1$H-NMR (270 MHz, CDCl$_3$) δ (ppm): 7.80-7.71 (211, m), 7.52-7.38 (3H, m), 0.25 (18H, s)

Synthesis of Example Compound 30

Example Compound 30 was synthesized in the same manner as the Example Compound 2, except that methylphosphonic acid dimethyl ester was changed to vinylphosphonic acid diethyl ester and the conditions of the vacuum-distillation were changed to 78 to 82° C./0.8 kPa (yield: 73%). The result of $^1$H-NMR measurement of the Example Compound 30 is shown below.

$^1$H-NMR (270 MHz, CDCl$_3$) δ (ppm): 6.12-5.76 (3H, m), 0.23 (18H, s)

Synthesis of Example Compound 31

Example Compound 31 was synthesized in the same manner as the Example Compound 2, except that methylphosphonic acid dimethyl ester was changed to 1-propenylphosphonic acid diethyl ester and the conditions of the vacuum-distillation were changed to 62 to 69° C./0.2 kPa (yield: 79%). The result of $^1$H-NMR measurement of the Example Compound 31 is shown below.

$^1$H-NMR (270 MHz, CDCl$_3$) δ (ppm): 6.63-6.41 (1H, m), 5.79-5.65 (1H, ddd, J=27, 17, 1.6 Hz), 1.83-1.79 (3H, m), 0.23 (18H, s)

Synthesis of Example Compound 34

Example Compound 34 was synthesized in the same manner as the Example Compound 2, except that methylphosphonic acid dimethyl ester was changed to (trimethylsilyldifluoromethyl)phosphonic acid diethyl ester and the conditions of the vacuum-distillation were changed to 95 to 103° C./0.1 kPa (yield: 40%). The result of $^1$H-NMR measurement of the Example Compound 34 is shown below.

$^1$H-NMR (270 MHz, CDCl$_3$) δ (ppm): 0.26 (18H, s), 0.19 (9H, s)

Synthesis of Example Compound 57

Example Compound 57 was synthesized in the same manner as the Example Compound 2, except that methylphosphonic acid dimethyl ester was changed to (trimethylsilyloxymethyl)phosphonic acid diethyl ester and the conditions of the vacuum-distillation were changed to 61 to 71° C./0.2 kPa (yield: 84%). The result of $^1$H-NMR measurement of the Example Compound 57 is shown below.

$^1$H-NMR (270 MHz, CDCl$_3$) δ (ppm): 3.71-3.67 (2H, d, J=8.9 Hz), 0.23 (18H, s), 0.08 (9H, s)

Synthesis of Example Compound 109

Example Compound 109 was synthesized in the same manner as the Example Compound 2, except that methylphosphonic acid dimethyl ester was changed to methylenediphosphonic acid tetraethyl ester, that the amount of trimethylsilyl bromide was increased to 6 eq. and that the conditions of the vacuum-distillation were changed to 118 to 123° C./0.2 kPa (yield: 89%). The result of $^1$H-NMR measurement of the Example Compound 109 is shown below.

$^1$H-NMR (270 MHz, CDCl$_3$) δ (ppm): 2.32-2.16 (2H, t, J=21.6 Hz), 0.25 (36H, s)

Synthesis of Example Compound 169

A mixed solution of methylphosphonic acid (12 mmol, 1.15 g) and 1,3-diethoxy-1,1,3,3-tetramethyl disiloxane (10 mmol, 2.22 g) was heated at 100° C. for 3 hours. The resulting reaction solution was vacuum-distilled (141 to 145° C./0.1 kPa) to obtain Example Compound 169 (yield: 0.63 g, 23%/methylphosphonic acid). The result of $^1$H-NMR measurement of the Example Compound 169 is shown below.

$^1$H-NMR (270 MHz, CDCl$_3$) δ (ppm): 1.54-1.47 (3H, d, J=18.4 Hz), 0.23 (18H, s)

Example 1

A lithium secondary battery was prepared by the following procedures.

Preparation of Negative Electrode

First, 20 parts by mass of an artificial graphite, 80% by mass of a natural graphite-based graphite, 1 part by mass of carboxymethyl cellulose and 2 parts by mass of SBR latex were kneaded in an aqueous solvent to prepare a negative electrode mixture slurry in the form of a paste.

Then, after coating and drying the thus obtained negative electrode mixture slurry on a negative electrode collector made of a band-shaped copper foil having a thickness of 18 μm, the resultant was compressed using a roll press to obtain a sheet-form negative electrode composed of the negative electrode collector and a negative electrode active material layer. Here, the negative electrode active material layer had a coating density of 10 mg/cm$^2$ and a packing density of 1.5 g/ml.

Preparation of Positive Electrode

First, 90 parts by mass of LiMn$_2$O$_4$, 5 parts by mass of acetylene black and 5 parts by mass of polyvinylidene fluoride were kneaded using N-methylpyrrolidinone as a solvent to prepare a positive electrode mixture slurry in the form of a paste.

Then, after coating and drying the thus obtained positive electrode mixture slurry on a positive electrode collector made of a band-shaped aluminum foil having a thickness of 20 μm, the resultant was compressed using a roll press to obtain a sheet-form positive electrode composed of the positive electrode collector and a positive electrode active material layer. Here, the positive electrode active material layer had a coating density of 30 mg/cm$^2$ and a packing density of 2.5 g/ml.

Preparation of Non-Aqueous Electrolyte Solution

As a non-aqueous solvent, ethylene carbonate (EC), dimethyl carbonate (DMC) and methylethyl carbonate (EMC) were mixed at a ratio of 34:33:33 (mass ratio) to obtain a mixed solvent.

In the thus obtained mixed solvent, LiPF$_6$ as an electrolyte was dissolved such that the LiPF$_6$ concentration in the eventually obtained non-aqueous electrolyte solution became 1.0 mol/L.

Then, to the thus obtained solution, Example Compound 2 was added as an additive such that the content thereof in the eventually obtained non-aqueous electrolyte solution became 0.5% by mass.

Preparation of Coin-Type Battery

The above-described negative and positive electrodes were punched out in the form of disks having a diameter of 14 mm and 13 mm, respectively, to obtain coin-shaped electrodes. Furthermore, a separator was obtained by punching out a 20 μm-thick microporous polyethylene film in the form of a disk having a diameter of 17 mm.

The thus obtained coin-shaped negative electrode, separator and coin-shaped positive electrode were laminated in this order in a stainless steel battery can (size 2032) and 20 μl of the above-described non-aqueous electrolyte solution was injected thereinto to impregnate the separator and the positive and negative electrodes with the non-aqueous electrolyte solution.

Furthermore, an aluminum plate (1.2 min in thickness, 16 mm in diameter) and a spring were placed on the positive electrode and the battery was then sealed by caulking the battery can lid via a polypropylene gasket, thereby preparing a coin-type lithium secondary battery having a diameter of 20 mm, a height of 3.2 mm and the configuration shown in FIG. 1 (hereinafter, referred to as "test battery").

For the thus obtained coin-type battery (test battery), the initial characteristics and the characteristics after high-temperature storage were evaluated.

Evaluation Methods

Evaluation of Battery Initial Characteristics and Characteristics After High-Temperature Storage The test battery was charged at a constant voltage of 4.0 V. Then, the thus charged test battery was cooled to −10° C. in a thermostat chamber and the impedance thereof was measured using impedance measuring apparatuses manufactured by Solartron (POTENTIOGALVANOSTAT SU 287 and FREQUENCY RESPONSE ANALYZER 1255B). Here, the resistance [Ω] at 0.2 Hz was defined as the initial battery resistance.

The results are shown in Table 1 below.

After the impedance measurement, the test battery was charged at a constant current of 1 mA and a constant voltage of 4.2 V in a 25° C. thermostat chamber. Subsequently, in this 25° C. thermostat chamber, the battery was allowed to discharge to 2.85 V at a constant current of 1 mA and the discharge capacity before high-temperature storage [mAh] was measured.

Then, after charging the above-described test battery at a constant current of 1 mA and a constant voltage of 4.2 V in the 25° C. thermostat chamber, the temperature of the thermostat chamber was raised to 80° C. and the test battery was stored for two days in the 80° C. thermostat chamber (high-temperature storage).

After the high-temperature storage, the temperature of the thermostat chamber was returned to 25° C. and in this 25° C. thermostat chamber, the test battery was allowed to discharge to 2.85 V at a constant current of 1 mA to measure the residual discharge capacity of the battery [mAh] (that is, the discharge capacity after high-temperature storage [mAh]) was measured.

Thereafter, using the following equation, the capacity retention rate before and after high-temperature storage was calculated.

Capacity retention rate before and after high-temperature storage [%]=(Discharge capacity after high-temperature storage [mAh]/Discharge capacity before high-temperature storage [mAh])×100 [%]

Examples 2 to 12

Non-aqueous electrolyte solutions were prepared and coin-type batteries were obtained in the same manner as in Example 1, except that the respective Example Compounds (3, 5, 8, 19, 30, 31, 34, 57, 95, 109 and 169) listed in the "Additive" column of Table 1 were added in place of the above-described Example Compound 2.

For the thus obtained coin-type batteries, the initial characteristics and the characteristics after high-temperature storage were evaluated in the same manner as in Example 1. The results are summarized in Table 1 below.

The names and structures of the Examples Compounds 2, 3, 5, 8, 19, 30, 31, 34, 57, 95, 109 and 169 are shown below. In these structures of the Example Compounds shown below, "Me" and "Ph" represent a methyl group and a phenyl group, respectively.

Example Compounds

Example Compound 2: methylphosphonic acid bis(trimethylsilyl) ester

Example Compound 3: methylphosphonic acid bis(tert-butyldimethylsilyl) ester

Example Compound 5: methylphosphonic acid bis(allyldimethylsilyl) ester

Example Compound 8: methylphosphonic acid bis(triphenylsilyl) ester

Example Compound 19: phenylphosphonic acid bis(trimethylsilyl) ester

Example Compound 30: vinylphosphonic acid bis(trimethylsilyl) ester

Example Compound 31: 1-propenylphosphonic acid bis(trimethylsilyl) ester

Example Compound 34: [difluoro(trimethylsilyl)methyl]phosphonic acid bis(trimethylsilyl) ester Example Compound 57: [(trimethylsilyloxy)methyl]phosphonic acid bis(trimethylsilyl) ester Example Compound 95: [(methanesulfonyl-oxy)methyl]phosphonic acid bis(trimethylsilyl) ester Example Compound 109: methylenebisphosphonic acid tetrakis(trimethylsilyl) ester Example Compound 169:
2,4,4,6,6-pentamethyl-1,3,5-trioxa-2-phospha-4,6-disila-cyclohexane-2-oxide

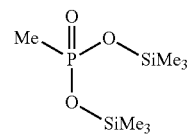
(Example Compound 2)

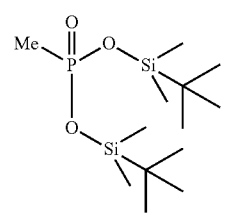
(Example Compound 3)

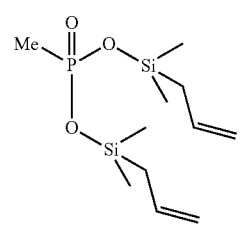
(Example Compound 5)

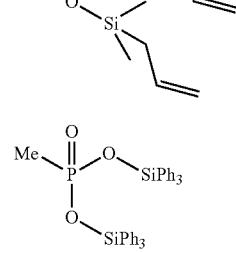
(Example Compound 8)

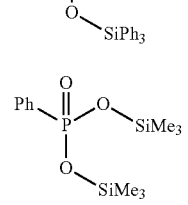
(Example Compound 19)

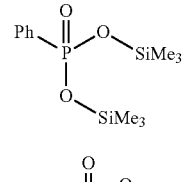
(Example Compound 30)

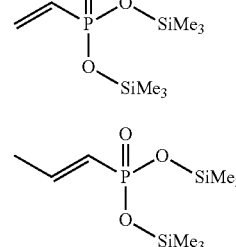
(Example Compound 31)

-continued

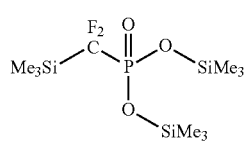
(Example Compound 34)

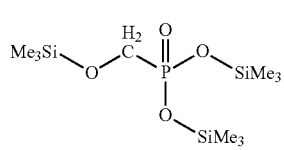
(Example Compound 57)

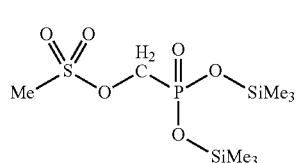
(Example Compound 95)

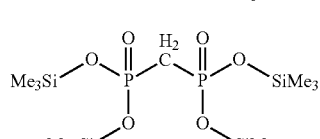
(Example Compound 109)

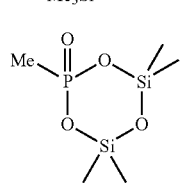
(Example Compound 169)

Example 13

A non-aqueous electrolyte solution was prepared and a coin-type battery was obtained in the same manner as in Example 1 except that, in the preparation of the non-aqueous electrolyte solution of Example 1, LiBF$_4$ was further added such that the LiBF$_4$ concentration in the eventually obtained non-aqueous electrolyte solution became 0.01 mol/L. For the thus obtained coin-type battery, the initial characteristics and the characteristics after high-temperature storage were evaluated in the same manner as in Example 1.

The results are summarized in Table 1 below.

Comparative Examples 1 to 14

In Comparative Example 1, a non-aqueous electrolyte solution was prepared and a coin-type battery was obtained in the same manner as in Example 1, except that the above-described Example Compound 2 was not added.

Furthermore, in Comparative Examples 2 to 13, non-aqueous electrolyte solutions were prepared and coin-type batteries were obtained in the same manner as in Example 1, except that the respective Comparative Compounds shown below were added in place of the above-described Example Compound 2.

It is noted here that, in these Comparative Compounds shown below, "Me", "Et" and "Ph" represent a methyl group, an ethyl group and a phenyl group, respectively.

In Comparative Example 14, a non-aqueous electrolyte solution was prepared and a coin-type battery was obtained in the same manner as in Example 1, except that the above-described Example Compound 2 was not added and LiBF$_4$ was added such that the LiBF$_4$ concentration in the eventually obtained non-aqueous electrolyte solution became 0.01 mol/L.

For the thus obtained coin-type batteries, the initial characteristics and the characteristics after high-temperature storage were evaluated in the same manner as in Example 1. The results are summarized in Table 1 below in the same manner as those of Examples.

Comparative Compounds

Comparative Compound A: methylphosphonic acid

Comparative Compound B: methylphosphonic acid dimethyl ester

Comparative Compound C: phenylphosphonic acid

Comparative Compound D: phenylphosphonic acid dimethyl ester

Comparative Compound E: vinylphosphonic acid

Comparative Compound F: vinylphosphonic acid diethyl ester

Comparative Compound G: 1-propenylphosphonic acid diethyl ester

Comparative Compound H: (trimethylsilyldifluoromethyl)phosphonic acid diethyl ester Comparative Compound I: (trimethylsilyloxy-methyl) phosphonic acid diethyl ester Comparative Compound J: (methanesulfonyloxy-methyl) phosphonic acid diethyl ester Comparative Compound K: methylenediphosphonic acid tetraethyl ester Comparative Compound L: tris(trimethylsilyl)phosphate The Comparative Compounds A to L have the following structures.

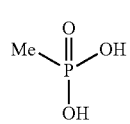
(Comparative Compound A)

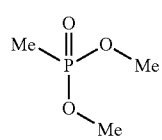
(Comparative Compound B)

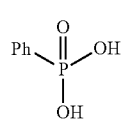
(Comparative Compound C)

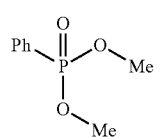
(Comparative Compound D)

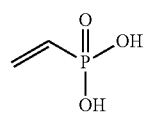
(Comparative Compound E)

-continued

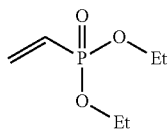
(Comparative Compound F)

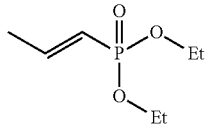
(Comparative Compound G)

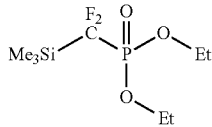
(Comparative Compound H)

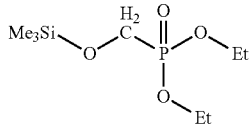
(Comparative Compound I)

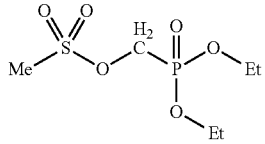
(Comparative Compound J)

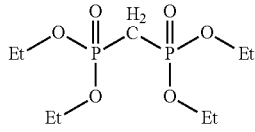
(Comparative Compound K)

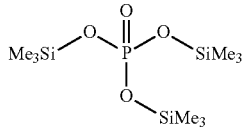
(Comparative Compound L)

Example 14

A non-aqueous electrolyte solution was prepared and a coin-type battery was obtained in the same manner as in Example 1 except that, in the preparation of the non-aqueous electrolyte solution of Example 1, the Example Compound 2 and vinylene carbonate (VC) were added as additives such that the contents thereof in the eventually obtained non-aqueous electrolyte solution each became 0.5% by mass. For the thus obtained coin-type battery, the initial characteristics and the characteristics after high-temperature storage were evaluated in the same manner as in Example 1. The results are summarized in Table 2 below.

Examples 15 to 25

Non-aqueous electrolyte solutions were prepared and coin-type batteries were obtained in the same manner as in Example 14, except that the respective Example Compounds (3, 5, 8, 19, 30, 31, 34, 57, 95, 109 and 169) were added in place of the above-described Example Compound 2. For the thus obtained coin-type batteries, the initial characteristics and the characteristics after high-temperature storage were evaluated in the same manner as in Example 14. The results are summarized in Table 2 below.

Example 26

A non-aqueous electrolyte solution was prepared and a coin-type battery was obtained in the same manner as in Example 14 except that, in the preparation of the non-aqueous electrolyte solution of Example 14, $LiBF_4$ was further added such that the $LiBF_4$ concentration in the eventually obtained non-aqueous electrolyte solution became 0.01 mol/L. For the thus obtained coin-type battery, the initial characteristics and the characteristics after high-temperature storage were evaluated in the same manner as in Example 14. The results are summarized in Table 2 below.

Comparative Examples 15 to 28

In Comparative Example 15, a non-aqueous electrolyte solution was prepared and a coin-type battery was obtained in the same manner as in Example 14, except that the above-described Example Compound 2 was not added.

Furthermore, in Comparative Examples 16 to 27, non-aqueous electrolyte solutions were prepared and coin-type batteries were obtained in the same manner as in Example 14, except that the above-described respective Comparative Compounds A to L were added in place of the above-described Example Compound 2.

In Comparative Example 28, a non-aqueous electrolyte solution was prepared and a coin-type battery was obtained in the same manner as in Example 14, except that the above-described Example Compound 2 was not added and $LiBF_4$ was added such that the $LiBF_4$ concentration in the eventually obtained non-aqueous electrolyte solution became 0.01 mol/L.

For the thus obtained coin-type batteries, the initial characteristics and the characteristics after high-temperature storage were evaluated in the same manner as in Example 14. The results are summarized in Table 2 below in the same manner as those of Examples.

TABLE 1

|  | Electrolyte (mol/L) | Additive | Battery resistance [Ω] | Discharge capacity after high-temperature storage [mAh] | Capacity retention rate after high-temperature storage [%] |
| --- | --- | --- | --- | --- | --- |
| Example 1 | $LiPF_6$(1.0) | Example Compound 2 0.5% by mass | 91 | 3.1 | 77 |
| Example 2 | $LiPF_6$(1.0) | Example Compound 3 0.5% by mass | 98 | 3.0 | 76 |

TABLE 1-continued

|  | Electrolyte (mol/L) | Additive | Battery resistance [Ω] | Discharge capacity after high-temperature storage [mAh] | Capacity retention rate after high-temperature storage [%] |
|---|---|---|---|---|---|
| Example 3 | $LiPF_6$(1.0) | Example Compound 5 0.5% by mass | 103 | 3.0 | 74 |
| Example 4 | $LiPF_6$(1.0) | Example Compound 8 0.5% by mass | 110 | 3.0 | 74 |
| Example 5 | $LiPF_6$(1.0) | Example Compound 19 0.5% by mass | 95 | 3.0 | 74 |
| Example 6 | $LiPF_6$(1.0) | Example Compound 30 0.5% by mass | 92 | 3.1 | 77 |
| Example 7 | $LiPF_6$(1.0) | Example Compound 31 0.5% by mass | 94 | 3.0 | 75 |
| Example 8 | $LiPF_6$(1.0) | Example Compound 34 0.5% by mass | 99 | 3.0 | 75 |
| Example 9 | $LiPF_6$(1.0) | Example Compound 57 0.5% by mass | 86 | 3.0 | 76 |
| Example 10 | $LiPF_6$(1.0) | Example Compound 95 0.5% by mass | 96 | 3.1 | 78 |
| Example 11 | $LiPF_6$(1.0) | Example Compound 109 0.5% by mass | 94 | 3.1 | 74 |
| Example 12 | $LiPF_6$(1.0) | Example Compound 169 0.5% by mass | 101 | 3.1 | 73 |
| Example 13 | $LiPF_6$(1.0) + $LiBF_4$ (0.01) | Example Compound 2 0.5% by mass | 84 | 3.1 | 76 |
| Comparative Example 1 | $LiPF_6$(1.0) | — | 177 | 2.8 | 70 |
| Comparative Example 2 | $LiPF_6$(1.0) | Comparative Compound A 0.5% by mass | 140 | 2.8 | 66 |
| Comparative Example 3 | $LiPF_6$(1.0) | Comparative Compound B 0.5% by mass | 151 | 2.9 | 68 |
| Comparative Example 4 | $LiPF_6$(1.0) | Comparative Compound C 0.5% by mass | 164 | 2.8 | 66 |
| Comparative Example 5 | $LiPF_6$(1.0) | Comparative Compound D 0.5% by mass | 113 | 2.9 | 68 |
| Comparative Example 6 | $LiPF_6$(1.0) | Comparative Compound E 0.5% by mass | 184 | 3.0 | 70 |
| Comparative Example 7 | $LiPF_6$(1.0) | Comparative Compound F 0.5% by mass | 235 | 2.9 | 67 |
| Comparative Example 8 | $LiPF_6$(1.0) | Comparative Compound G 0.5% by mass | 150 | 2.8 | 67 |
| Comparative Example 9 | $LiPF_6$(1.0) | Comparative Compound H 0.5% by mass | 136 | 3.0 | 68 |
| Comparative Example 10 | $LiPF_6$(1.0) | Comparative Compound I 0.5% by mass | 121 | 2.7 | 64 |
| Comparative Example 11 | $LiPF_6$(1.0) | Comparative Compound J 0.5% by mass | 132 | 2.9 | 67 |
| Comparative Example 12 | $LiPF_6$(1.0) | Comparative Compound K 0.5% by mass | 138 | 2.8 | 66 |

TABLE 1-continued

|  | Electrolyte (mol/L) | Additive | Battery resistance [Ω] | Discharge capacity after high-temperature storage [mAh] | Capacity retention rate after high-temperature storage [%] |
|---|---|---|---|---|---|
| Comparative Example 13 | LiPF$_6$(1.0) | Comparative Compound L 0.5% by mass | 94 | 3.0 | 71 |
| Comparative Example 14 | LiPF$_6$(1.0) + LiBF$_4$ (0.01) | — | 95 | 2.9 | 68 |

TABLE 2

|  | Electrolyte (mol/L) | Additive | | Battery resistance [Ω] | Discharge capacity after high-temperature storage [mAh] | Capacity retention rate after high-temperature storage [%] |
|---|---|---|---|---|---|---|
| Example 14 | LiPF$_6$(1.0) | VC 0.5% by mass | Example Compound 2 0.5% by mass | 83 | 3.3 | 82 |
| Example 15 | LiPF$_6$(1.0) | VC 0.5% by mass | Example Compound 3 0.5% by mass | 89 | 3.2 | 81 |
| Example 16 | LiPF$_6$(1.0) | VC 0.5% by mass | Example Compound 5 0.5% by mass | 94 | 3.2 | 79 |
| Example 17 | LiPF$_6$(1.0) | VC 0.5% by mass | Example Compound 8 0.5% by mass | 96 | 3.2 | 79 |
| Example 18 | LiPF$_6$(1.0) | VC 0.5% by mass | Example Compound 19 0.5% by mass | 86 | 3.2 | 79 |
| Example 19 | LiPF$_6$(1.0) | VC 0.5% by mass | Example Compound 30 0.5% by mass | 84 | 3.3 | 82 |
| Example 20 | LiPF$_6$(1.0) | VC 0.5% by mass | Example Compound 31 0.5% by mass | 85 | 3.2 | 80 |
| Example 21 | LiPF$_6$(1.0) | VC 0.5% by mass | Example Compound 34 0.5% by mass | 90 | 3.2 | 80 |
| Example 22 | LiPF$_6$(1.0) | VC 0.5% by mass | Example Compound 57 0.5% by mass | 78 | 3.2 | 81 |
| Example 23 | LiPF$_6$(1.0) | VC 0.5% by mass | Example Compound 95 0.5% by mass | 87 | 3.3 | 83 |
| Example 24 | LiPF$_6$(1.0) | VC 0.5% by mass | Example Compound 109 0.5% by mass | 85 | 3.3 | 83 |
| Example 25 | LiPF$_6$(1.0) | VC 0.5% by mass | Example Compound 169 0.5% by mass | 92 | 3.3 | 79 |
| Example 26 | LiPF$_6$ (1.0) + LiBF$_4$ (0.01) | VC 0.5% by mass | Example Compound 2 0.5% by mass | 76 | 3.3 | 81 |
| Comparative Example 15 | LiPF$_6$(1.0) | VC 0.5% by mass | — | 125 | 2.8 | 72 |
| Comparative Example 16 | LiPF$_6$(1.0) | VC 0.5% by mass | Comparative Compound A 0.5% by mass | 122 | 2.8 | 68 |
| Comparative Example 17 | LiPF$_6$(1.0) | VC 0.5% by mass | Comparative Compound B 0.5% by mass | 131 | 2.9 | 70 |
| Comparative Example 18 | LiPF$_6$(1.0) | VC 0.5% by mass | Comparative Compound C 0.5% by mass | 143 | 2.8 | 68 |
| Comparative Example 19 | LiPF$_6$(1.0) | VC 0.5% by mass | Comparative Compound D 0.5% by mass | 98 | 2.9 | 70 |

TABLE 2-continued

| | Electrolyte (mol/L) | | Additive | Battery resistance [Ω] | Discharge capacity after high-temperature storage [mAh] | Capacity retention rate after high-temperature storage [%] |
|---|---|---|---|---|---|---|
| Comparative Example 20 | LiPF$_6$ (1.0) | VC 0.5% by mass | Comparative Compound E 0.5% by mass | 160 | 3.0 | 72 |
| Comparative Example 21 | LiPF$_6$ (1.0) | VC 0.5% by mass | Comparative Compound F 0.5% by mass | 204 | 2.9 | 69 |
| Comparative Example 22 | LiPF$_6$ (1.0) | VC 0.5% by mass | Comparative Compound G 0.5% by mass | 130 | 2.8 | 69 |
| Comparative Example 23 | LiPF$_6$ (1.0) | VC 0.5% by mass | Comparative Compound H 0.5% by mass | 118 | 3.0 | 70 |
| Comparative Example 24 | LiPF$_6$ (1.0) | VC 0.5% by mass | Comparative Compound I 0.5% by mass | 105 | 2.7 | 66 |
| Comparative Example 25 | LiPF$_6$ (1.0) | VC 0.5% by mass | Comparative Compound J 0.5% by mass | 115 | 2.9 | 69 |
| Comparative Example 26 | LiPF$_6$ (1.0) | VC 0.5% by mass | Comparative Compound K 0.5% by mass | 120 | 2.8 | 68 |
| Comparative Example 27 | LiPF$_6$ (1.0) | VC 0.5% by mass | Comparative Compound L 0.5% by mass | 82 | 3.0 | 73 |
| Comparative Example 28 | LiPF$_6$ (1.0) + LiBF$_4$ (0.01) | VC 0.5% by mass | — | 83 | 2.9 | 70 |

From the results shown in Table 1, comparing Examples 1 to 12 where the silyl ester group-containing compound of the present invention was added and Comparative Example 1 where the compound of the present invention was not added, it is seen that, by adding the compound of the present invention, the battery resistance, which is an initial characteristic, can be reduced and a high capacity retention rate after high-temperature storage can be attained. From these results, it is understood that an addition of the compound of the present invention contributes to an extended battery service life.

Furthermore, focusing on the ester group of phosphonic acid derivative, from comparisons between a silyl ester group-containing compound of the present invention (Example Compound 2) and a compound in which the silyl ester group is substituted with an OH group (Comparative Compound A) as well as a compound in which the silyl ester group is substituted with an alkyl ester group (Comparative Compound B), it is seen that, by adding the compound of the present invention, the battery resistance, which is an initial characteristic, can be reduced and a high capacity retention rate after high-temperature storage can be attained. From these results, it is understood that an addition of a silyl ester group shown in the present invention contributes to an extended battery service life.

In Comparative Example 13 where Comparative Compound L, which is silyl ester group-substituted phosphoric acid, was used, although an effect of reducing the initial battery resistance could be confirmed, the capacity retention rate after high-temperature storage was lower than that of those cases where the compound of the present invention was used; therefore, it is seen that the silyl ester group-containing phosphonic acid derivative according to the present invention is useful.

Paying attention to Examples 1 and 13 and Comparative Example 14, it is seen that a further reduction in the battery resistance could be achieved by further adding LiBF$_4$ to the compound of the present invention as compared to those cases where LiBF$_4$ was not added.

Meanwhile, when LiBF$_4$ was solely added, although a reduction in the battery resistance could be attained, the capacity retention rate after high-temperature storage was not improved (Comparative Example 14). From these results, it is seen that an addition of the silyl ester group-containing phosphonic acid derivative according to the present invention and a tetrafluoroborate contributes to an extended battery service life.

These effects of the compound of the present invention explained with reference to the results shown in Table 1 can also be confirmed from the results in Table 2 in the same manner.

Furthermore, as clearly seen from comparisons between Examples 1 to 13 in Table 1 and Examples 14 to 26 in Table 2, by using the compound of the present invention and VC in combination, the battery resistance, which is an initial characteristic, can be further reduced and the capacity retention rate after high-temperature storage can be further improved.

The entire disclosure of Japanese Patent Application No. 2010-117404 is incorporated in this specification by reference.

All publications, patent applications, and technical standards described in this specification are herein incorporated by reference to the same extent as if each individual publication, patent application, or technical standard was specifically and individually indicated to be incorporated by reference.

The invention claimed is:

1. A non-aqueous electrolyte solution, comprising a silyl ester group-containing phosphonic acid derivative.

2. The non-aqueous electrolyte solution according to claim 1, wherein the silyl ester group-containing phosphonic acid derivative is a compound represented by the following the Formula (1):

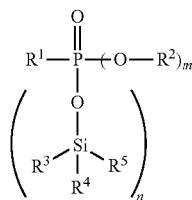

wherein, in the Formula (1), m represents 0 or 1; n represents 1 or 2; m+n=2;

R¹ represents a hydrogen atom, an alkyl group having 1 to 12 carbon atoms, a haloalkyl group having 1 to 12 carbon atoms, an aryl group having 6 to 14 carbon atoms (which may be substituted with a halogen atom, an alkyl group having 1 to 6 carbon atoms or a haloalkyl group having 1 to 6 carbon atoms), an alkenyl group having 2 to 12 carbon atoms, an alkyl group having 1 to 6 carbon atoms, which is substituted with at least one —SiR¹⁸R¹⁹R²⁰ group (wherein R¹⁸, R¹⁹ and R²⁰ each independently represent an alkyl group having 1 to 6 carbon atoms, an alkenyl group having 2 to 6 carbon atoms, an alkoxy group having 1 to 6 carbon atoms or a phenyl group), a haloalkyl group having 1 to 6 carbon atoms, which is substituted with at least one —SiR¹⁸R¹⁹R²⁰ group (wherein R¹⁸, R¹⁹ and R²⁰ each independently represent an alkyl group having 1 to 6 carbon atoms, an alkenyl group having 2 to 6 carbon atoms, an alkoxy group having 1 to 6 carbon atoms or a phenyl group), a 5- or 6-membered heterocyclic group (which may or may not be substituted), or a group represented by any one of the following Formulae (3-1) to (3-10);

R² represents a hydrogen atom, an alkyl group having 1 to 6 carbon atoms, a haloalkyl group having 1 to 6 carbon atoms, an alkenyl group having 2 to 6 carbon atoms, or a phenyl group (which may be substituted with a halogen atom, an alkyl group having 1 to 6 carbon atoms or a haloalkyl group having 1 to 6 carbon atoms);

R³ represents an alkyl group having 1 to 6 carbon atoms, an alkenyl group having 2 to 6 carbon atoms, an alkoxy group having 1 to 6 carbon atoms, a phenyl group, a —O—SiR⁶R⁷R⁸ group (wherein R⁶, R⁷ and R⁸ each independently represent an alkyl group having 1 to 6 carbon atoms, an alkenyl group having 2 to 6 carbon atoms, an alkoxy group having 1 to 6 carbon atoms or a phenyl group), or a group in which, when n is 2, two R³s are linked with each other to form —O—, an alkylene group having 1 to 3 carbon atoms or —O—(SiR¹⁶R¹⁷—O)_p— (wherein R¹⁶ and R¹⁷ independently represent an alkyl group having 1 to 6 carbon atoms, an alkenyl group having 2 to 6 carbon atoms, an alkoxy group having 1 to 6 carbon atoms or a phenyl group; and p represents an integer of 1 to 3); and R⁴ and R⁵ each independently represent an alkyl group having 1 to 6 carbon atoms, an alkenyl group having 2 to 6 carbon atoms, an alkoxy group having 1 to 6 carbon atoms, a phenyl group or a —O—SiR⁶R⁷R⁸ group (wherein R⁶, R⁷ and R⁸ each independently represent an alkyl group having 1 to 6 carbon atoms, an alkenyl group having 2 to 6 carbon atoms, an alkoxy group having 1 to 6 carbon atoms or a phenyl group):

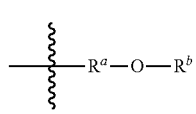
(3-1)

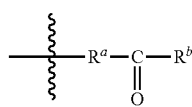
(3-2)

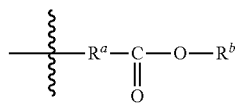
(3-3)

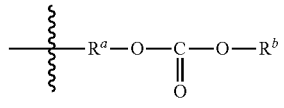
(3-4)

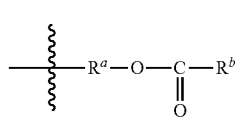
(3-5)

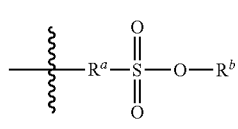
(3-6)

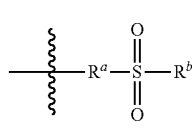
(3-7)

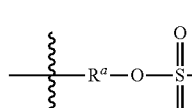
(3-8)

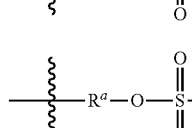
(3-9)

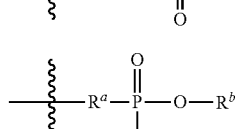
(3-10)

wherein, in Formulae (3-1) to (3-10), $R^a$ represents a divalent hydrocarbon group having 1 to 12 carbon atoms which may be substituted with a halogen atom; and $R^b$ represents a hydrocarbon group having 1 to 12 carbon atoms which may be substituted with a halogen atom, or a —SiR²¹R²²R²³ group (wherein R²¹, R²² and R²³ each independently represent an alkyl group having 1 to 6 carbon atoms, an alkenyl group having 2 to 6 carbon atoms, an alkoxy group having 1 to 6 carbon atoms or a phenyl group).

3. The non-aqueous electrolyte solution according to claim 2, wherein m is 0 and n is 2 in the Formula (1).

4. The non-aqueous electrolyte solution according to claim 3, wherein, in the Formula (1), $R^1$ is an alkyl group having 1 to 6 carbon atoms, a fluoroalkyl group having 1 to 6 carbon atoms, an aryl group having 6 to 14 carbon atoms (which may be substituted with a fluorine atom, an alkyl group having 1 to 6 carbon atoms or a fluoroalkyl group having 1 to 6 carbon atoms), an alkenyl group having 2 to 6 carbon atoms, an alkyl group having 1 to 6 carbon atoms, which is substituted with one —$SiR^{18}R^{19}R^{20}$ group (wherein $R^{18}$, $R^{19}$ and $R^{20}$ each independently represent an alkyl group having 1 to 6 carbon atoms, an alkenyl group having 2 to 6 carbon atoms, an alkoxy group having 1 to 6 carbon atoms or a phenyl group), a fluoroalkyl group having 1 to 6 carbon atoms, which is substituted with one —$SiR^{18}R^{19}R^{20}$ group (wherein $R^{18}$, $R^{19}$ and $R^{20}$ each independently represent an alkyl group having 1 to 6 carbon atoms, an alkenyl group having 2 to 6 carbon atoms, an alkoxy group having 1 to 6 carbon atoms or a phenyl group), a 5- or 6-membered heterocyclic group (wherein the heterocyclic group is a furyl group, a thienyl group, a pyrrolyl group, an oxazolyl group, an isoxazolyl group, a thiazolyl group, an isothiazolyl group, an imidazolyl group, a pyrazolyl group, a triazolyl group, a tetrazolyl group, a pyridyl group, a pyrimidinyl group, a pyrazinyl group, a pyridazinyl group or a triazinyl group and may be substituted with a fluorine atom, an alkyl group having 1 to 6 carbon atoms or a fluoroalkyl group having 1 to 6 carbon atoms), or a group represented by any one of the Formulae (3-1), (3-9) and (3-10), with the proviso that, in the Formulae (3-1), (3-9) and (3-10), $R^a$ is an alkylene group having 1 to 6 carbon atoms, a fluoroalkylene group having 1 to 6 carbon atoms, a phenylene group (which may be substituted with a fluorine atom, an alkyl group having 1 to 6 carbon atoms or a fluoroalkyl group having 1 to 6 carbon atoms) or an alkenylene group having 2 to 6 carbon atoms, and $R^b$ is an alkyl group having 1 to 6 carbon atoms, a fluoroalkyl group having 1 to 6 carbon atoms, a phenyl group (which may be substituted with a fluorine atom, an alkyl group having 1 to 6 carbon atoms or a fluoroalkyl group having 1 to 6 carbon atoms), an alkenyl group having 2 to 6 carbon atoms, or a —$SiR^{21}R^{22}R^{23}$ group (wherein $R^{21}$, $R^{22}$ and $R^{23}$ are each independently an alkyl group having 1 to 6 carbon atoms, an alkenyl group having 2 to 6 carbon atoms, an alkoxy group having 1 to 6 carbon atoms or a phenyl group).

5. The non-aqueous electrolyte solution according to claim 3, wherein, in the Formula (1), $R^1$ is an alkyl group having 1 to 6 carbon atoms, a fluoroalkyl group having 1 to 6 carbon atoms, an aryl group having 6 to 14 carbon atoms (which may be substituted with a fluorine atom, an alkyl group having 1 to 6 carbon atoms or a fluoroalkyl group having 1 to 6 carbon atoms), an alkenyl group having 2 to 6 carbon atoms, an alkyl group having 1 to 6 carbon atoms, which is substituted with one —$SiR^{18}R^{19}R^{20}$ group (wherein $R^{18}$, $R^{19}$ and $R^{20}$ are each independently an alkyl group having 1 to 6 carbon atoms), a fluoroalkyl group having 1 to 6 carbon atoms, which is substituted with one —$SiR^{18}R^{19}R^{20}$ group (wherein $R^{18}$, $R^{19}$ and $R^{20}$ are each independently an alkyl group having 1 to 6 carbon atoms), or a group represented by any one of the Formulae (3-1), (3-9) and (3-10), with the proviso that, in the Formulae (3-1), (3-9) and (3-10), $R^a$ is an alkylene group having 1 to 6 carbon atoms and $R^b$ is an alkyl group having 1 to 6 carbon atoms or a —$SiR^{21}R^{22}R^{23}$ group (wherein $R^{21}$, $R^{22}$ and $R^{23}$ are each independently an alkyl group having 1 to 6 carbon atoms); and $R^3$, $R^4$ and $R^5$ are each independently an alkyl group having 1 to 6 carbon atoms, an alkenyl group having 2 to 6 carbon atoms or a phenyl group.

6. The non-aqueous electrolyte solution according claim 3, wherein the compound represented by the Formula (1) is methylphosphonic acid bis(trimethylsilyl) ester, methylphosphonic acid bis(tert-butyldimethylsilyl) ester, methylphosphonic acid bis(allyldimethylsilyl) ester, methylphosphonic acid bis(triphenylsilyl) ester, phenylphosphonic acid bis(trimethylsilyl) ester, vinylphosphonic acid bis(trimethylsilyl) ester, 1-propenylphosphonic acid bis(trimethylsilyl) ester, [difluoro(trimethylsilyl)methyl]phosphonic acid bis(trimethylsilyl) ester, [(trimethylsilyloxy)methyl]phosphonic acid bis(trimethylsilyl) ester, [(methanesulfonyl-oxy)methyl]phosphonic acid bis(trimethylsilyl) ester, methylenebisphosphonic acid tetrakis(trimethylsilyl) ester, or 2,4,4,6,6-pentamethyl-1,3,5-trioxa-2-phospha-4,6-disilacyclohexane-2-oxide.

7. The non-aqueous electrolyte solution according to claim 2, wherein the content of the silyl ester group-containing phosphonic acid derivative is 0.001% by mass to 10% by mass.

8. The non-aqueous electrolyte solution according to claim 2, further comprising a tetrafluoroborate.

9. The non-aqueous electrolyte solution according to claim 8, wherein the tetrafluoroborate is lithium tetrafluoroborate ($LiBF_4$).

10. The non-aqueous electrolyte solution according to claim 8, wherein the concentration of the tetrafluoroborate is 0.0001 mol/L to 2 mol/L.

11. A lithium secondary battery, comprising:

a positive electrode;

a negative electrode containing, as a negative electrode active material, at least one selected from lithium metal, lithium-containing alloys, metals or alloys that are capable of forming an alloy with lithium, oxides capable of doping/dedoping lithium ions, transition metal nitrides capable of doping/dedoping lithium ions and carbon materials capable of doping/dedoping lithium ions; and the non-aqueous electrolyte solution according to claim 2.

12. A lithium secondary battery, which is obtained by charging/discharging a lithium secondary battery comprising:

a positive electrode;

a negative electrode containing, as a negative electrode active material, at least one selected from lithium metal, lithium-containing alloys, metals or alloys that are capable of forming an alloy with lithium, oxides capable of doping/dedoping lithium ions, transition metal nitrides capable of doping/dedoping lithium ions and carbon materials capable of doping/dedoping lithium ions; and the non-aqueous electrolyte solution according to claim 2.

* * * * *